US010300144B2

(12) United States Patent
Jain et al.

(10) Patent No.: US 10,300,144 B2
(45) Date of Patent: May 28, 2019

(54) N-TERMINAL POLYSIALYLATION

(75) Inventors: Sanjay Jain, London (GB); Rongsheng Zhang, London (GB)

(73) Assignee: Lipoxen Technologies Limited, London (GB)

( * ) Notice: Subject to any disclaimer, the term of this patent is extended or adjusted under 35 U.S.C. 154(b) by 582 days.

(21) Appl. No.: 12/375,010

(22) PCT Filed: Jul. 25, 2007

(86) PCT No.: PCT/GB2007/002821
§ 371 (c)(1),
(2), (4) Date: Jul. 30, 2009

(87) PCT Pub. No.: WO2008/012528
PCT Pub. Date: Jan. 31, 2008

(65) Prior Publication Data
US 2010/0022441 A1    Jan. 28, 2010

(30) Foreign Application Priority Data

Jul. 25, 2006  (EP) .................................... 06117830

(51) Int. Cl.
| A61K 47/61 | (2017.01) |
| A61K 38/18 | (2006.01) |
| C07K 14/535 | (2006.01) |
| C07K 14/52 | (2006.01) |
| C07K 14/505 | (2006.01) |
| C07K 14/575 | (2006.01) |
| A61K 38/46 | (2006.01) |
| A61K 38/19 | (2006.01) |
| C12N 9/22 | (2006.01) |
| A61K 38/00 | (2006.01) |

(52) U.S. Cl.
CPC .......... *A61K 47/61* (2017.08); *A61K 38/1816* (2013.01); *A61K 38/193* (2013.01); *A61K 38/465* (2013.01); *C07K 14/505* (2013.01); *C07K 14/52* (2013.01); *C07K 14/535* (2013.01); *C07K 14/575* (2013.01); *C12N 9/22* (2013.01); *C12Y 301/21001* (2013.01); *A61K 38/00* (2013.01); *Y02A 50/473* (2018.01)

(58) Field of Classification Search
None
See application file for complete search history.

(56) References Cited

U.S. PATENT DOCUMENTS

| 5,679,645 | A | 10/1997 | Ikeuchi et al. |
| 5,824,784 | A | 10/1998 | Kinstler et al. |
| 5,846,951 | A | 12/1998 | Gregoriadis |
| 6,323,311 | B1 | 11/2001 | Liu et al. |
| 6,956,027 | B2 | 10/2005 | Kinstler |
| 6,962,972 | B2 * | 11/2005 | Gregoriadis ................. 530/345 |
| 7,074,755 | B2 | 7/2006 | Heavner |
| 7,128,913 | B2 | 10/2006 | Burg et al. |
| 7,807,824 | B2 * | 10/2010 | Jain et al. ..................... 536/123 |
| 7,875,708 | B2 * | 1/2011 | Jain et al. ..................... 536/17.2 |
| 2004/0082765 | A1 | 4/2004 | Nakamura et al. |
| 2007/0014759 | A1 | 1/2007 | DeFrees et al. |
| 2007/0083006 | A1 * | 4/2007 | Hinds et al. ................. 525/54.1 |
| 2007/0191597 | A1 | 8/2007 | Jain et al. |

FOREIGN PATENT DOCUMENTS

| CA | 1156217 | 11/1983 | |
| EP | 0 550 108 | 7/1993 | |
| EP | 1 219 636 | 7/2003 | |
| EP | 1681303 | 7/2006 | |
| JP | 2003-533537 | 11/2003 | |
| RU | 2 141 531 | 11/1999 | |
| WO | WO 1991/005867 | 5/1991 | |
| WO | WO-92/22331 | 12/1992 | |
| WO | WO 1999/043307 | 2/1999 | |
| WO | WO 01/87922 A2 * | 11/2001 | ............. A61K 38/00 |
| WO | WO 2001/087272 | 11/2001 | |
| WO | WO-2001/087922 | 11/2001 | |
| WO | WO 2003/031464 | 4/2003 | |
| WO | WO 2003/055526 | 7/2003 | |
| WO | WO-2004/091494 | 10/2004 | |
| WO | WO 2004091494 A * | 10/2004 | ............. A61K 38/00 |
| WO | WO 2004/101619 | 11/2004 | |
| WO | WO 2005/003149 | 1/2005 | |

(Continued)

OTHER PUBLICATIONS

Jain Set al: "Polysialylated insulin: synthesis, characterization and biological activity in vivo" BBA—General Subjects, Elsevier Science Publishers, NL, vol. 1622, No. 1,Jun. 20, 2003 (Jun. 20, 2003), pp. 42-49, XP004433607 ISSN: 0304-41 65.*

Gregoriadis et al: "Improving the therapeutic efficacy of peptides and proteins: A role for polysialic acids" International Journal of Pharmaceutics, Amsterdam, NL, vol. 300, No. 1-2, Aug. 26, 2005 (Aug. 26, 2005), pp. 125-130, XP005013268 ISSN: 0378-5173.*

Br© wnlee Met al: "A Glucose Controlled Insulin Delivery System Semi Synthetic Insulin Bound to Lectin" Science (Washington D C), vol. 206, No. 4423, 1979, pp. 1190-1191, XP002461920 ISSN: 0036-8075.*

Sato Met al: "Site-specific introduction of sialic acid into insulin" Angewandte Chemie. International Edition, Wiley VCH Verlag, Weinheim, DE, vol. 43, No. 12, Mar. 12, 2004 (Mar. 12, 2004), pp. 1516-1520, XP002981412 ISSN: 1433-7851.*

(Continued)

*Primary Examiner* — Maury A Audet

(74) *Attorney, Agent, or Firm* — Entralta P.C.; Jeffrey M. McQuiston; Peter D. Weinstein

(57) ABSTRACT

The present invention relates to a composition comprising a population of polysaccharide derivatives of a protein, wherein the protein is insulin or an insulin-like protein and the polysaccharide is anionic and comprises between 2 and 125 saccharide units, and wherein the population consists of substantially only N-terminal derivatives of the protein. Typically, the polysaccharide is PSA. The present invention also relates to pharmaceutical compositions comprising the novel compounds, and methods for making the novel compounds.

23 Claims, 15 Drawing Sheets

(56) References Cited

FOREIGN PATENT DOCUMENTS

| WO | WO-05/016973 | | | 2/2005 | | |
|---|---|---|---|---|---|---|
| WO | WO 2005/014050 | | | 2/2005 | | |
| WO | WO-2005/016974 | | | 2/2005 | | |
| WO | WO 2005016974 | A | * | 2/2005 | ............ | A61K 38/00 |
| WO | WO 2005/037320 | | | 4/2005 | | |
| WO | WO 2005/055946 | | | 6/2005 | | |
| WO | WO-06/016161 | | | 2/2006 | | |
| WO | WO-2006/016168 | | | 2/2006 | | |
| WO | WO 2006016168 | A2 | * | 2/2006 | ............ | C08B 37/00 |
| WO | WO 2006/000540 | | | 5/2006 | | |
| WO | WO 2006/074467 | | | 7/2006 | | |
| WO | WO-06/090119 | | | 8/2006 | | |
| WO | WO-2006/082184 | | | 8/2006 | | |
| WO | WO-2007/047922 | | | 4/2007 | | |
| WO | WO 2008/12540 | | | 1/2008 | | |

OTHER PUBLICATIONS

Uchio et al. "Site-specific insulin conjugates with enhanced stability and extended action profile." Advanced Drug Delivery Reviews vol. 35, Issues 2-3, Feb. 1, 1999, pp. 289-306.*
Caliceti and Veronese, S.T.P. Pharma Sciences (1999) 9(1):107-113.
Ehrat and Luisi, Biopolymers (1983) 22:569-573.
Fernandes and Gregoriadis, Biochimica et Biophysica Acta (1996) 1293:90-96.
Fernandes and Gregoriadis, Biochimica et Biophysica Acta (1997) 1341:26-34.
Geiger et al., Insulin: Chemistry, Structure, and Function of Insulin and Related Hormones, Branderburg and Wollmer, (eds.), Waiter de Gruyter & Co., New York (1980) pp. 409-415.
Gregoriadis et al., FEBS Letters (1993) 315:271-276.
Hinds et al., Bioconjugate Chemistry (2000) 11:195-201 (abstract only).
Hinds and Kim, Advanced Drug Delivery Reviews (2002)54:505-530.
Park and Johnson, Journal of Biological Chemistry (1949) 181:149-151.
Svennerholm, Biochimica et Biophysica Acta (1957) 24:604-611.
Uchio et al., Advanced Drug Delivery Reviews (1999) 35:289-306.
Wang, International Journal of Pharmaceutics (1999) 185:129-188.
Brownlee et al., Science (1979) 206(4423):1190-1191.
Gregoriadis et al., Intl J Pharmaceutics (2005) 300(1-2):125-130.
International Preliminary Report on Patentability and Written Opinion of the International Searching Authority for PCT/GB2007/002821, dated Jan. 27, 2009, 7 pages.
International Search Report for PCT/GB2007/002821, dated Dec. 21, 2007, 3 pages.
Jain et al., Biochim Biophys Acta (2003) 1622(1):42-49.
Sato et al., Angewandte Chemie, Intl Edition (2004) 43(12):1516-1520.
Almeida et al., Solid lipid nanoparticles as a drug delivery system for peptides and proteins., Advance Drug Delivery Reviews, 2007 (59): 478-490.
Defrees S. et al., "GlycoPEGylation of recombinant therapeutic proteins produced in *Escherichia coli*.", Glycobiology. Sep. 2006;16(9):833-43. Epub May 22, 2006.
Fan Q. et al., "Preclinical evaluation of Hematide, a novel erythropoiesis stimulating agent, for the treatment of anemia.", Exp Hematol. Oct. 2006;34(10):1303-11.
Jain et al., Polysialylation: the natural way to improve the stability and pharmacokinetics of protein and peptide drugs., Drug Delivery Systems and Science, 2004, 4(1):3-9.
Kinstler et al., Mono-N-terminal poly(ethylene glycol)-protein conjugates., Advance Drug Delivery Reviews, 2002 54(4):477-485.
Krystal, A Simple Microassay for Erythropoietin Based on H-Thymidine Incorporation into Spleen Cells from Phenylhydrazine Treated Mice., 1983 11(7):649-660.
Lifely et al., Sialic Acid Polysaccharide Antigens of Neisseria meningitis and *Escherichia coli*; Esterification Between Adjacent Residues., 1981 (94):193-203.
Molineux G., "The design and development of pegfilgrastim (PEG-rmetHuG-CSF, Neulasta)", Curr Pharm Des. 2004;10(11):1235-44.
Shafer et al., Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides., 2000 Vaccines 18:1273-1281.
Sinicropi et al., Colorimetric Determination of DNase I Activity with a DNA-Methyl Green Substrate., 1994 (222):351-358.
Zhang et al., Obestatin, a peptide encoded by the ghrelin gene, opposes ghrelin's effects on food intake., Science. Nov. 11, 2005;310(5750):996-9.
P. Cuatrecasas, "Interaction of Insulin with the Cell Membrane: The Primary Action of Insulin." PNAS, v. 63, No. 2, Jun. 1969.
Sato et al., "Glycoinsulins: Dendritic Sialyloligosaccharide-Displaying Insulins Showing a Prolonged Blood-Sugar-Lowering Activity." J. of American Chemical Society, v. 126, No. 43, pp. 14013-14022, Nov. 11, 2004.
European Search Report EP 13 15 3525 dated Oct. 16, 2013.

* cited by examiner

N-TERMINAL POLYSIALYLATION

CROSS-REFERENCE TO RELATED APPLICATIONS

This application is the national phase of PCT application PCT/GB2007/002821 having an international filing date of 25 Jul. 2007, which claims benefit of European patent application No. 06117830.7 filed 25 Jul. 2006. The contents of the above patent applications are incorporated by reference herein in their entirety.

The present invention relates to novel polysaccharide derivatives of insulin and methods for producing such derivatives. The derivatives are useful for improving the stability, pharmacokinetics and pharmacodynamics of insulin.

Diabetes is a disorder of carbohydrate metabolism and results from insufficient production of, or reduced sensitivity to, insulin. Insulin is synthesized in the beta cells of the islets of Langerhans of the pancreas and is necessary for normal utilization of glucose by most cells in the body. In persons with diabetes, the normal ability to use glucose is inhibited, thereby increasing blood sugar levels (hyperglycemia).

There are two varieties of the diabetes. Type I is insulin-dependent diabetes mellitus, or IDDM. IDDM was formerly referred to as juvenile onset diabetes. In IDDM, insulin is not secreted by the pancreas and must be provided from an external source. Type II adult-onset diabetes can ordinarily be controlled by diet although in some advanced cases insulin is required.

Before the isolation of insulin in the 1920s, most patients died within a short time after onset of the disease. Untreated diabetes leads to ketosis, the accumulation of ketones (products of fat breakdown) in the blood; this is followed by acidosis (accumulation of acid in the blood) with nausea and vomiting. As the toxic products of disordered carbohydrate and fat metabolism continue to build up, the patient goes into diabetic coma.

Treatment of diabetes typically requires regular injections of insulin. This results in a dramatic, life-saving clinical improvement. Due to the inconvenience of insulin injections, however, insulin has been the focus of massive efforts to improve its administration and bioassimilation.

The insulin molecule consists of two chains of amino acids linked by disulfide bonds (mw 5804). The [beta]-cells of the pancreatic islets secrete a single chain precursor of insulin, known as proinsulin. Proteolysis of proinsulin results in removal of four basic amino acids (numbers 31, 32, 64 and 65 in the proinsulin chain: Arg, Arg, Lys, Arg respectively) and the connecting ("C") polypeptide. In the resulting two-chain insulin molecule, the A chain has glycine at the amino terminus, and the B chain has phenylalanine at the amino terminus.

Insulin may exist as a monomer, dimer or a hexamer formed from three of the dimers. The hexamer is coordinated with two $Zn^{2+}$ atoms. Biological activity resides in the monomer. Although until recently bovine and porcine insulin were used almost exclusively to treat diabetes in humans, numerous variations in insulin between species are known. Porcine insulin is most similar to human insulin, from which it differs only in having an alanine rather than threonine residue at the B-chain C-terminus. Despite these differences most mammalian insulin has comparable specific activity. Until recently animal extracts provided all insulin used for treatment of the disease. The advent of recombinant technology allows commercial scale manufacture of human insulin (e.g., Humulin™ insulin, commercially available from Eli Lilly and Company, Indianapolis, Ind.).

Attempts have been made to derivatise insulin to improve its pharmacokinetic properties. There is a product on the market, PEG-insulin (Nektar Therapeutics). PEG is a neutral, water-soluble, nontoxic polymer comprising any number of repeating units of ethylene oxide. PEGylation is designed to increase the size of the active molecule and ultimately improve drug performance by optimising pharmacokinetics, increasing bioavailability, and decreasing immunogenicity and dosing frequency. The design and development of PEG-insulin is described further in WO2004091494.

A variety of methods for producing PEGylated insulin derivatives are known. Davis et al. (U.S. Pat. No. 4,179,337) describe the synthesis of a PEG-insulin construct using trichloro-s-triazine (cyanuric chloride) as the linker between PEG and protein. They follow a synthetic scheme in which a large excess (50×) of cyanuric chloride activated PEG (2000 Da) was reacted with insulin in borate buffer (pH 9.2) for 2 hours. The inventors were able to produce partially active (about 50%) PEG-insulin conjugates, which were non-immunogenic and non-antigenic. Obermeier et al. (Canadian Patent No. 1,156,217), found that preparation of PEG-insulin conjugates according to the Davis patent referenced above produced a non-uniform mixture of conjugates containing approximately 50% tri-PEG-insulin, and the other possible PEG-insulin derivative combinations (mono- and di-PEG-insulins) were not substituted at residue PheB1.

Obermeier et al. (Canadian Patent No. 1,156,217) describe synthesis of PEG-insulin conjugates specifically modified at residue PheB1. The basis of their invention involves protecting the reactive amines at residues GlyA1 and LysB29 with tert-butyloxycarbonyl (t-boc) or methylsulfonylethyloxycarbonyl (Msc) groups in organic solvents (e.g., DMF, DMSO, pyridine, etc.) under alkaline conditions. From the complex mixture of (mono-, di-, and tri-) protected insulins the N.sup..alpha.A1, N.sup..epsilon.B29-bis-protected-insulin species was isolated by conventional chromatographic techniques. Following isolation, the pure N.sup..alpha.A1, N.sup..epsilon.B29-bis-protected-insulin was reacted with an activated (e.g., acid chloride or isocyanate) PEG derivative with subsequent removal of the protecting groups using techniques common to peptide chemistry. The inventors observed that the amino groups of GlyA1 and LysB29 were more reactive than PheB1's amino group under alkaline reaction conditions. They determined their site-specific mPEG(1500)-B1-insulin conjugates had a 100% insulin effect (calculated on a molar basis) on reduction of blood sugar levels in rabbits.

Geiger et al. (1980) and Ehrat et al. (1983) describe PEG-insulin adducts specifically modified at residue PheB1 prepared utilizing a protection/conjugation/deprotection scheme similar to the multi-step method described by Obermeier et al, Geiger et al. and Ehrat et al. and observed that the PEG(1500)-B1-insulin conjugate was far less antigenic and far more stable (to liver enzymes) than native insulin. Other PEG-insulin preparations (Caliceti et al., 1999; Uchio et al., 1999; Hinds et al., 2002 are either: 1) centered on the basic three-step protection/conjugation/deprotection schemes outlined above, 2) result in non-specific modification of the insulin molecule, or 3) do not produce the most effective conjugates, namely, PEG-B1-insulins.

Liu et al. (U.S. Pat. No. 6,323,311 B1) describe a useful method for the synthesis of PEG-B1-insulin conjugates. This method is an extension of the Obermeier three-step protection/conjugation/deprotection scheme, but does not require the isolation of reaction intermediates between steps (i.e., one-pot synthesis). Thus, the insulin is protected at residues GlyA1 and LysB29, immediately reacted with PEG, and subsequently deprotected before any isolation of species. The inventors claim that their one-pot reaction may yield up to 50% of the correct positional isomer (i.e. PEG-B1-insulin) and 30% unreacted insulin that can be recycled for subsequent derivatization. Assuming the preparation of these constructs is carried out expeditiously, it would take at least five days to completion. In addition, the invention requires large excesses of the PEG reagent to achieve acceptable results. While the products of this invention may be effective, their preparation still requires the protein to undergo three reaction steps in protein-adverse environments (high and low pH) for extended periods of time.

The invention in US2007083006 addresses the shortcomings of prior art methods for PEGylating insulins by providing a method for the simple preparation of highly pure insulin derivatives specifically PEGylated at the N-terminus of insulin's B-chain (PheB1) in a single-step. In contrast to prior experience (e.g., Caliceti et al., 1999, supra) indicating that PEGylation at PheB1 is the least probable reaction product, the present method employs specific conditions of pH control, use of a metal ion chelator and addition of organic solvent to enhance the relative reactivity of the PheB1 amino terminus to where it becomes the predominant site of PEGylation. Considering the numerous beneficial properties imparted on insulin (e.g., decreased immunogenicity/antigenicity; increased proteolytic, chemical and physical stability; increased circulation half-life; increased aqueous/organic solubility; full biological activity) via site-specific PEGylation at residue PheB1, a simple, cost-effective, and easily scalable process for achieving this result would be a significant advancement in the art.

In view of the prior art, there is a need to provide improved derivatives of insulin which can be used in human and animal therapy and have optimised stability, half lives and low toxicity. We have found that attaching PSAs to insulin imparts such properties.

Polysialic acids (PSAs) are naturally occurring unbranched polymers of sialic acid produced by certain bacterial strains and in mammals in certain cells. They can be produced in various degrees of polymerisation from n=about 80 or more sialic acid residues down to n=2 by limited acid hydrolysis or by digestion with neuraminidases, or by fractionation of the natural, bacterially derived forms of the polymer.

In recent years, the biological properties of polysialic acids, particularly those of the alpha-2,8 linked homopolymeric polysialic acid, have been exploited to modify the pharmacokinetic properties of protein and low molecular weight drug molecules. Polysialic acid derivatisation gives rise to dramatic improvements in circulating half-life for a number of therapeutic proteins including catalase and asparaginase, and also allows such proteins to be used in the face of pre-existing antibodies raised as an undesirable (and sometimes inevitable) consequence of prior exposure to the therapeutic protein [Fernandes and Gregoriadis, 1996, 1997]. The alpha-2,8 linked polysialic acid offers an attractive alternative to PEG, being an immunologically invisible biodegradable polymer which is naturally part of the human body, and which degrades, via tissue neuraminidases, to sialic acid, a non-toxic saccharide.

We have previously described methods for the attachment of polysaccharides (in particular PSA) to therapeutic agents such as proteins [U.S. Pat. No. 5,846,951; WO-A-0187922]. Some of these methods depend upon chemical derivatisation of the 'non-reducing' end of the polymer to create a protein-reactive aldehyde moiety which reacts at primary amine groups. A non-reducing sialic acid terminal unit, since it contains vicinal diols, can be readily (and selectively) oxidised with periodate to yield a mono-aldehyde form, which is much more reactive towards proteins, and which comprises a suitably reactive element for the attachment of proteins via reductive amination and other chemistries. The reaction is illustrated in FIGS. 1 and 2 wherein FIG. 1 shows the oxidation of colominic acid (alpha-2,8 linked polysialic acid from *E. coli*) with sodium periodate to form a protein-reactive aldehyde at the non-reducing end; and FIG. 2 shows the selective reduction of the Schiff's base with sodium cyanoborohydride to form a stable irreversible covalent bond with the protein amino group.

The inventors have described in previous publications, for instance in Biochimica et Biophysica Acta (2003), the synthesis of polysialylated insulin. In this reference 22 kDa and 39 kDa colominic acid are oxidised and reacted with amino groups of recombinant human insulin. The polydispersity of the CAs used is 1.33 and 1.40, which is too large for therapeutic use.

We have also described in our previous patent application, published as WO2005/016974, the synthesis of insulin-colominic acid conjugates. However, in this application, the conjugates are not all specifically N-terminal, and a variety of conjugates are produced.

Unintentional by-products may be generated during the conventional conjugation reactions described above by reaction of the colominic acid with side chains of amino acids, for instance. These may be sufficient to be troublesome in the manufacture of chemically defined conjugates required by regulatory authorities for therapeutic use in man and animals.

It is not straightforward to purify the intended reaction product (for instance the monopolysialylated product) away from the various unintended products, since the physico-chemical characteristics of most of the reaction products are similar. This means that techniques such as ion-exchange chromatography and gel-permeation chromatography (which separate on the basis of charge and size respectively) produce poor purification profiles.

In accordance with a first aspect of this invention we provide a composition comprising a population of polysaccharide derivatives of a protein, wherein the protein is insulin or an insulin-like protein and the polysaccharide is anionic and comprises between 2 and 125 saccharide units, and wherein the population consists substantially only of N-terminal derivatives of the protein.

Hereinafter, when using the term insulin, we also intend to cover insulin-like proteins. By insulin-like protein, we mean a protein which has an activity equivalent to that of insulin. Insulin typically decreases blood glucose concentration. It also increases cell permeability to monosacchlorides, amino acids and fatty acids, and accelerates glycolysis, the pentose phosphate cycle, and glycogen synthesis in the liver. Preferably, the insulin-like protein has at least 35% more preferably at least 50% of the activity of human insulin derived from Swissprot accession number P01308.

Mutants of insulin which have the requisite activity, as detailed above, may also be used. An "insulin-like" protein may also be referred to as an "insulin-homologue". Whether two sequences are homologous is routinely calculated using a percentage similarity or identity, terms that are well known in the art. Sequences should be compared to SEQ I.D. No. 1 which is the unprocessed precursor of human insulin. Residues 25-54 correspond to the insulin B chain and residues 90-110 correspond to the insulin A chain. Homologue sequences may also be compared to the active form of human insulin.

Homologues preferably have 50% or greater similarity or identity at the nucleic acid or amino acid level, more preferably 60%, 70%, 80% or greater, more preferably 90% or greater, such as 95% or 99% identity or similarity at the nucleic acid or amino acid level. A number of programs are available to calculate similarity or identity; preferred programs are the BLASTn, BLASTp and BLASTx programs, run with default parameters, available at www.ncbi.nlm.nih.gov. For example, 2 amino acid sequences may be compared using the BLASTn program with default parameters (score=100, word length=11, expectation value=11, low complexity filtering=on). The above levels of homology are calculated using these default parameters.

The insulin may be natural, i.e. derived from a human or animal, or synthetic, for instance made by a recombinant method.

As is well known in the art, insulin comprises two peptide chains. Preferably, in this invention the insulin is derivatised with the polysaccharide at the N-terminus of its B chain.

By "population" we mean that there is more than one polysaccharide derivative in the composition. The derivatives may comprises the same or different numbers of saccharide units. Preferably, the polydispersity of the polysaccharide in the composition is less than 1.3, more preferably less than 1.1.

In the population, substantially all of the proteins are derivatised at the N-terminal only. Since there are two peptide chains in insulin there are two N terminal units. Preferably at least 85%, more preferably at least 90%, most preferably at least 95% of the B chains in the population are derivatised at the N-terminus with anionic polysaccharide. The N-terminus of the A chains need not be derivatised.

The degree of derivatisation at the N-terminus may be determined using standard techniques in the art, such as peptide mapping or Edman Degradation.

Preferably, the polysaccharide has at least 2, more preferably at least 5, most preferably at least 10, for instance at least 50 saccharide units.

The anionic polysaccharide is preferably selected from polysialic acid, heparin, hyaluronic acid and chondroitin sulphate. Preferably, the polysaccharide is polysialic acid and consists substantially only of sialic acid units. However, the polysaccharide may have units other than sialic acid in the molecule. For instance, sialic acid units may alternate with other saccharide units. Preferably, however, the polysaccharide consists substantially of units of sialic acid.

Preferably the polysaccharide has a terminal sialic acid group, and as detailed above, is more preferably a polysialic acid, that is a polysaccharide comprising at least 2 sialic acid units joined to one another through α-2-8 or α-2-9 linkages. A suitable polysialic acid has a weight average molecular weight in the range 2 to 100 kDa, preferably in the range 1 to 35 kDa. The most preferred polysialic acid has a molecular weight in the range of 10-20 kDa, typically about 14 kDa. Most preferably, the polysialic acid is derived from a bacterial source, for instance polysaccharide B of *E. coli* Kl, *N. meningitidis, Maraxella liquefaciens* or *Pasteurella aeruginosa* or K92 polysaccharide from *E. coli* K92 strain. It is most preferably colominic acid from *E. coli* K1.

The anionic polysaccharide, preferably polysialic acid may be in the form of a salt or the free acid. It may be in a hydrolysed form, such that the molecular weight has been reduced following recovery from a bacterial source. The polysaccharide, preferably polysialic acid may be material having a wide spread of molecular weights such as having a polydispersity of more than 1.3, for instance as much as 2 or more. Preferably the polydispersity of molecular weight is less than 1.3 or 1.2, preferably less than 1.1, for instance as low as 1.01.

Typically, the compound of this invention is a polysialic acid derivative of insulin and comprises 2-125 sialic acid units. More typically, the compound comprises 10-80 sialic acid units, preferably 20-60 sialic acid units, most preferably 40-50 sialic acid units.

The polysaccharide derivatives in the first aspect of this invention may be covalently-linked conjugates between the N-terminus of insulin and an anionic polysaccharide. Other means of association between the polysaccharide and the insulin include electrostatic attraction. However, covalent bonding is preferred. The covalent linkage may be an amide linkage between a carboxyl group and an amine group. Another linkage by which the insulin could be covalently bonded to the polysaccharide is via a Schiff base. Suitable groups for conjugating to amines are described further in WO 2006/016168.

In the invention the polysaccharide may be a naturally occurring polysaccharide, or a derivative of a naturally occurring polysaccharide, for instance, a polysaccharide which has been derivatised by a reaction of one or more active groups on the saccharide residues, or which has been covalently linked to a derivatising group at the end of the polysaccharide chain.

The polysaccharide may be linked to the insulin via either its reducing or non-reducing terminal unit.

Methods for attaching polysaccharides to proteins are well known in the art and are described in more detail in WO 92/22331 and WO-A-0187922. The preferred methods in this invention are described in more detail below. Methods are also described in FIGS. 1 and 2 of this application.

The polysaccharide may be linked to the insulin via its reducing and non-reducing terminal unit. This means that one polysaccharide chain may be linked to two insulin proteins, i.e. be derivatised at both its reducing and non-reducing end.

The polysaccharide may be linked to the insulin peptide directly, i.e. as shown in FIGS. 1 and 2, or via a linker. Suitable linkers are derived from N-maleimide, vinylsulphone, N-iodoacetamide, orthopyridyl or N-hydroxysuccinimide-containing reagents. The linker may also be biostable or biodegradable and comprise, for instance, a polypeptide or a synthetic oligomer. The linker may be derived from a bifunctional moiety, as further described in WO 2005/016973. A suitable bifunctional reagent is, for instance, Bis-NHS. The reagent may have general formula Z—R$^1$—Z wherein each Z is a functional group and may be the same or different and R$^1$ is a bifunctional organic radical. Preferably, R$^1$ is selected from the group consisting of alkanediyl, arylene, alkarylene, heteroarylene and alkylheteroarylene, any of which may substituted and/or interrupted by carbonyl, ester, sulfide, ether, amide and/or amine linkages. Particularly preferred is $C_3$-$C_6$ alkanediyl. Most preferably, R$^1$ corresponds to the appropriate portion of the suitable bifunctional reagent A preferred polysaccharide derivative is of general formula (I)

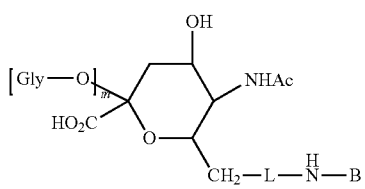 (I)

wherein m is at least one;

HNB is derived from B—NH$_2$ which is the N-terminus of insulin or a insulin-like peptide;

L is a bond, a linking group, or comprises a polypeptide or a synthetic oligomer;

GlyO is an anionic saccharide unit;

wherein the linking group, if present, is of general formula —Y—C(O)—R$^1$—C(O)—;

wherein Y is NR$^2$ or NR$^2$—NR$^2$ and R$^1$ is a difunctional organic radical as defined above; and R$^2$ is H or C$_{1-6}$ alkyl.

In this aspect of the invention the insulin is linked to the non-reducing end of the polysaccharide. The terminal polysaccharide unit is a sialic acid unit. The other saccharide units in the polysaccharide are represented by GlyO and may be the same or different. Suitable saccharide units include heparin, hyaluronic acid or chondroitin sulphate.

When the insulin is attached directly to the polysaccharide, the group L is a bond. However, the group L may alternatively be derived from an N-maleimide, vinylsulphone, N-iodoacetamide, orthopyridyl or N-hydroxysuccinimide containing reagent. The reagent may have general formula Z—R$^1$—Z as defined above. In this embodiment, L is typically a group

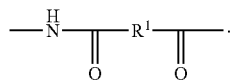

Another aspect of the invention is a composition as defined above which is a pharmaceutical composition and further comprises one or more pharmaceutically acceptable excipients.

The pharmaceutical composition may be in the form of an aqueous suspension. Aqueous suspensions contain the novel compounds in admixture with excipients suitable for the manufacture of aqueous suspensions. The pharmaceutical compositions may be in the form of a sterile injectable aqueous or homogeneous suspension. This suspension may be formulated according to the known art using suitable dispersing or wetting agents and suspending agents.

Pharmaceutical compositions may be administered orally, intravenously, intraperitoneally, intramuscularly, subcutaneously, intranasally, intradermally, topically or intratracheally for human or veterinary use.

The compositions may further comprise a formulation additive. By formulation additive we mean an excipient which is capable of stabilising the insulin either internally or externally, as described in Wang et al (1999). The excipient may be a stabiliser, a solubilser or a metal ion. Suitable examples of formulation additives include one or more buffers, stabilisers, surfactants, salts, polymers, metal ions, sugars, polyols or amino acids. These may be used alone or in combination.

Stabilisers typically act by destabilisation of the denatured state of a protein leading to increased Gibbs free energy change for unfolding of the protein. The stabiliser is preferably a sugar or a polyol, for example sucrose, sorbitol, trehalose, glycerol, mannitol, lactose and ethylene glycol. A stabilising buffer is sodium phosphate.

The solubiliser is preferably a surfactant, preferably a non-ionic surfactant. Suitable examples include Tween 80, Tween 20, Tween 40, Pluoronic F68, Brij 35 and Triton X100.

The metal ion is preferably divalent. Suitable metal ions include Zn2+, Ni$^{2+}$, Co$^{2+}$, Sr$^{2+}$, Cu$^{2+}$, Ca$^{2+}$, Mg$^{2+}$ and Fe$^{2+}$.

The formulation additive may also be a polymer selected from PSA, PEG or hydroxy-beta-cyclodextrin.

Preservatives such as m-Cresol may also be used.

Suitable amino acids and amino acid derivatives for use as the formulation additive include histidine, glycine, other similar amino acids and sodium aspartate.

A further aspect of the invention is a compound as described above for use in therapy.

In accordance with a further aspect of the invention, we provide a method for producing a polysaccharide derivative of insulin or of a insulin-like protein wherein an anionic polysaccharide comprising 2-125 saccharide units is chemically reacted substantially only at the N-terminal amine of the insulin or insulin-like protein.

The phase "chemically reacted substantially only at the N-terminal amine" means that in a population of derivatives at least 85%, more preferably at least 90%, most preferably at least 95% of the protein is derivatised only at its N-terminal amine. Preferably, this is at the N-terminal amine of the B chain of insulin.

Polysaccharide derivatives obtainable by this method, and any of the preferred embodiments, as detailed below, also form part of this invention.

We have developed a new method for conjugation of polysaccharides to proteins whereby the high reactivity of the N-terminal of the protein can be utilized and which avoids the product complexity obtained using the established method (FIGS. 1 and 2) of reductive amination of proteins with periodate oxidised natural colominic acid.

The polysaccharide may also react with a modified form of insulin. For instance, one or more groups on the insulin may have undergone a chemical transformation, for instance, by reduction or oxidation. A reactive carbonyl may be generated in the place of the terminal amino group of insulin using oxidation conditions, for instance.

Suitable polysaccharides for use in the method of this invention are as described previously for the novel compositions.

The compounds of the invention may be manufactured by any of the suitable methods described in the prior art. For example, a typical method is described to our previous patent application WO 92/22331.

Typically, the anionic polysaccharide has been activated before derivatisation to insulin. It may, for instance, have a reactive aldehyde group and the derivatisation reaction may be carried out under reducing conditions. The reactive aldehyde group may be produced by controlled oxidation of a hydroxyl group of the polysaccharide. Most preferably this reactive aldehyde is generated in a preliminary step, in which the polysaccharide is reacted under controlled oxidation conditions, for instance using sodium periodate, in aqueous solution. Preferably the oxidation is a chemical oxidation, although enzymes which are capable of carrying out this step may also be used. The reactive aldehyde group may be at the non-reducing end or reducing end of the polysaccharide. The insulin, typically the N-terminus, may then react with the reactive aldehyde group to produce an adduct which, when reduced, produces the N-terminal derivative of insulin.

The activation of the polysaccharide should preferably be carried out under conditions such that there is substantially no mid-chain cleavage of the backbone of the polysaccharide, that is substantially no molecular weight reduction. The oxidant is suitably perrhuthenate, or, preferably, periodate. Oxidation may be carried out with periodate at a concentration in the range 1 mM to 1M, at a pH in the range 3 to 10, a temperature in the range 0 to 60° C. for a time in the range 1 min to 48 hours.

Suitable reduction conditions for the derivatisation reaction may utilise hydrogen with catalysts or, preferably hydrides, such as borohydrides. These may be immobilised such as Amberlite (trade mark)-supported borohydride. Preferably alkali metal hydrides such as sodium borohydride is used as the reducing agent, at a concentration in the range 1 µM to 0.1M, a pH in the range 4 to 10, a temperature in the range 0 to 60° C. and a period in the range 1 min to 72 hours. The reaction conditions are selected such that pendant carboxyl groups on the starting material are not reduced. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Other activated derivatives of polysaccharides may have utility in the present invention, including those with pendant functional groups such as NHS, as described in our earlier patent application WO 06/00540.

In one embodiment, the reactive aldehyde is at the reducing end of the polysaccharide and the non-reducing end has been passivated such that it does not react with pendant groups on the insulin.

The reactivity of the reducing end of colominic acid, though weak towards protein targets, is sufficient to be troublesome in the manufacture of chemically defined conjugates.

Chemistry suitable for preparing a polysaccharide with a reactive aldehyde at the reducing terminal of a polysaccharide is described in our earlier application WO 05/016974. The process involves a preliminary selective oxidation step followed by reduction and then further oxidation to produce a compound with an aldehyde at the reducing terminal and a passivated non-reducing end.

WO 2005/016973 describes polysialic acid derivatives that are useful for conjugation to proteins, particularly those which have free sulfhydryl drugs. The polysialic acid compound is reacted with a heterobifunctional reagent to introduce a pendant functional group for site-specific conjugation to sulfhydryl groups. The anionic polysaccharides used in the present invention may also be derivatised with a heterobifunctional reagent in this manner.

The polysaccharide may be derivatised before it reacts with insulin. For instance, the polysaccharide may react with a bifunctional reagent.

The polysaccharide may be subjected to a preliminary reaction step, in which a group selected from a primary amine group, a secondary amine group and a hydrazine is formed on the terminal saccharide, which is preferably sialic acid, followed by a reaction step in which this is reacted with a bifunctional reagent to form a reaction-intermediate, as further described in WO 2006/016168. The intermediate may then react with the insulin or insulin-like peptide. The bifunctional reagent may have general formula Z—R$^1$—Z, as defined previously.

We have found that certain reaction conditions promote selective derivatisation at the N-terminal of the insulin. To promote selective reaction at the N-terminal, the derivatisation reaction should be carried out in a first aqueous solution of acidic pH, and the resultant polysaccharide derivative should then be purified in a second aqueous solution of higher pH than the first aqueous solution. By acidic pH we mean a pH less than 7. Typically the pH of the first aqueous solution is in the range 4.0-6.5, preferably 4.0-6.0 and the pH of the second aqueous solution is in the range of 6.5-9.0, preferably 6.5-8.5 or 6.5-8.0. The low pH of the derivatisation reaction promotes selective derivatisation at the N-terminus of the protein rather than at any mid-chain sites.

Furthermore, we have found that the use of certain formulation additives promotes the formation of a selective, stable, polysaccharide insulin-derivative. The formulation additive may be selected from one or more buffers, stabilisers, surfactants, salts, polymers, metal ions, sugars, polyols or amino acids. These may be added to the reaction medium, or alternatively may be added to the final product composition, as a stabiliser.

In one embodiment of this invention, the formulation additive is sorbitol, trehalose or sucrose. In a different embodiment, the formulation additive is a non-ionic surfactant. The formulation additive may alternatively be a polymer selected from PSA, PEG or hydroxy-beta-cyclodextrin. In a different embodiment the formulation additive is a divalent metal ion. Preferred divalent metal ions include $Zn^{2+}$, $Ni^{2+}$, $Co^{2+}$, $Sr^{2+}$ or $Fe^{2+}$.

The formulation additive may be a buffer. Preferably when the formulation additive is a buffer, it is sodium phosphate or sodium acetate.

The purification of the polysaccharide derivative in the method of the present invention may be carried out using a variety of methods known in the art. Examples of suitable purification methods include HIC (hydrophobic interaction chromatography), SEC (size exclusion chromatography), HPLC (high performance liquid chromatography), and IEC (ion exchange chromatography).

A population of polysialic acids having a wide molecular weight distribution may be fractionated into fractions with lower polydispersities, i.e. into fractions with differing average molecular weights. Fractionation is preferably performed by anion exchange chromatography, using for elution a suitable basic buffer, as described in our earlier patent applications WO 2005/016794 and WO 2005/03149. The fractionation method is suitable for a polysaccharide starting material as well as to the derivatives. The technique may thus be applied before or after the essential process steps of this invention. Preferably, the resultant polysaccharide derivative of insulin has a polydispersity of less than 1.1

The derivatisation of insulin in accordance with this invention, results in increased half life, improved stability, reduced immunogenicity, and/or control of solubility and hence bioavailability and the pharmacokinetic properties of insulin. The new method is of particular value for creation of a monopolysialylated-insulin conjugates.

The invention is illustrated by Examples 1-6 and by reference to the following drawings.

EXAMPLES

1. Protein and Colominic Acid Determination

Figure 1:
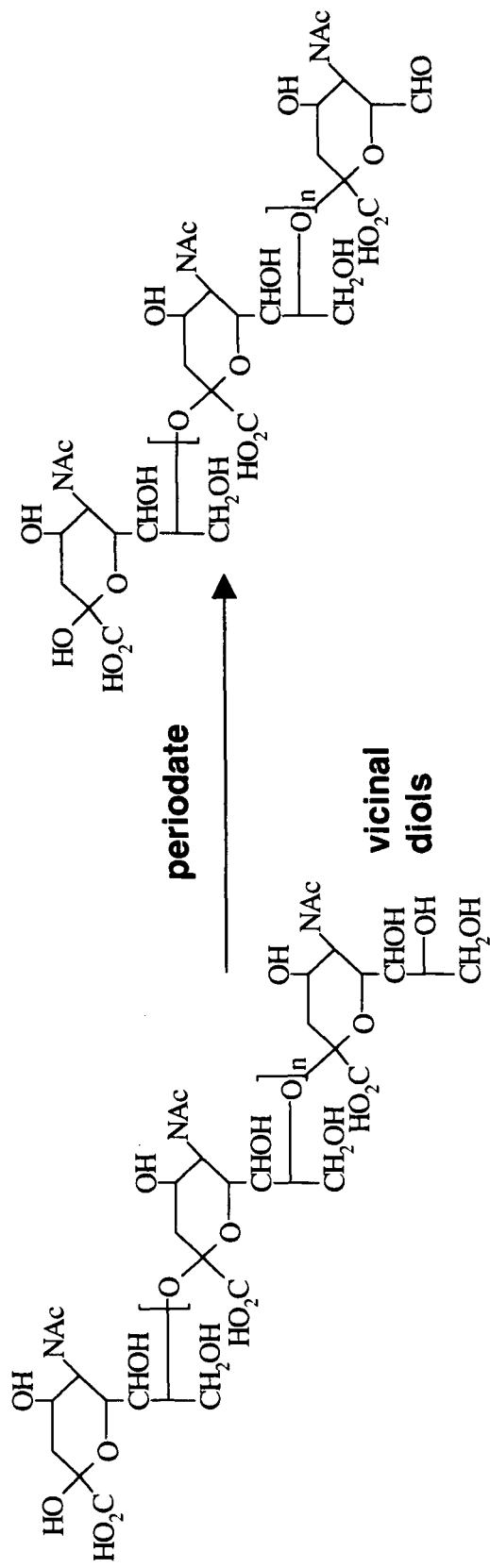
FIG. 1 shows the oxidation of colominic acid (alpha-2,8 linked polysialic acid from *E. coli*) with sodium periodate.
Figure 2:
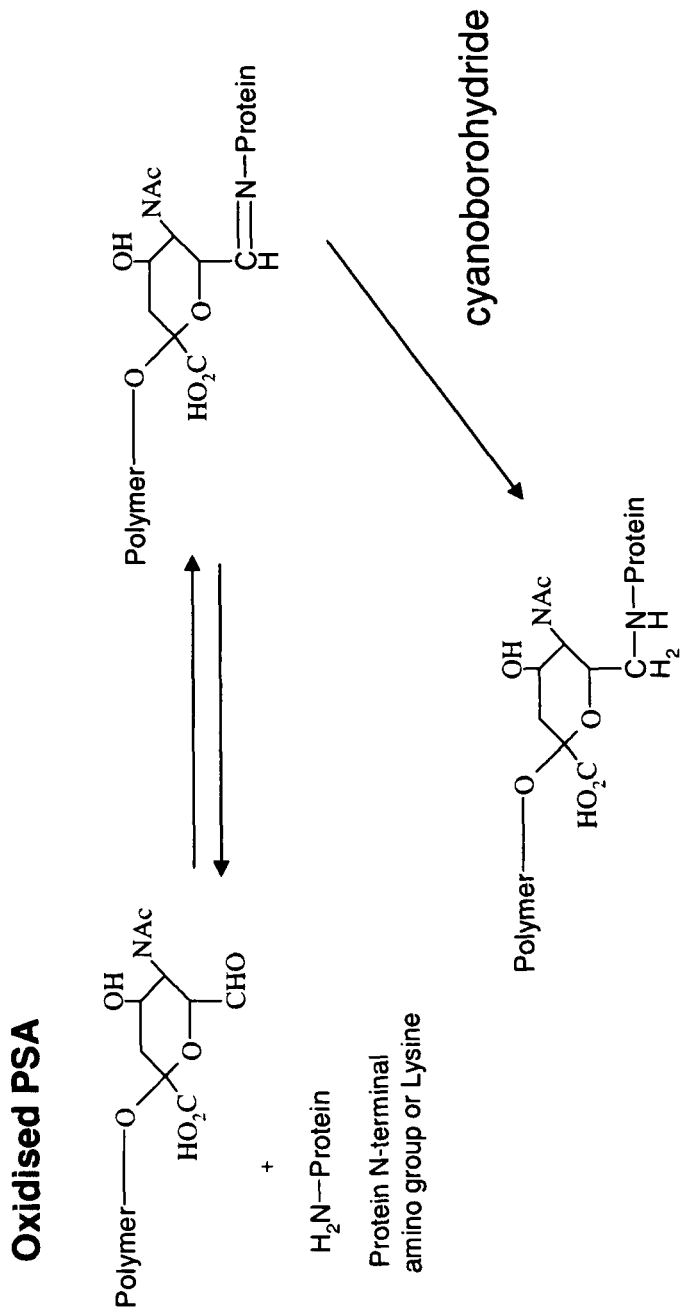
FIG. 2 shows the selective reduction of the Schiff's base with sodium cyanoborohydride to form a stable irreversible covalent bond with the protein amino group.

Quantitative estimation of polysialic acids (as sialic acid) with the resorcinol reagent was carried out by the resorcinol method [Svennerholm, 1957] as described elsewhere [Gregoriadis et al., 1993; Fernandes and Gregoriadis, 1996, 1997]. Protein was measured by the BCA colorimetric method or UV absorbance at 280 nm.

2. Activation of Colominic Acid

Freshly prepared 0.02 M sodium metaperiodate (NaIO4) solution (8 fold molar excess) was mixed with CA at 20° C. and the reaction mixture was stirred magnetically for 15 min in the dark. A two-fold volume of ethylene glycol was then added to the reaction mixture to expend excess $NaIO_4$ and the mixture left to stir at 20° C. for a further 30 min. The oxidised colominic acid (CAO) was dialysed (3.5 KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filterate was lyophilized and stored at −40° C. until further use. Alternatively, CAO was recovered from the reaction mixture by precipitation (twice) with ethanol.

3. Determination of the Oxidation State of Ca and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds. Non-oxidised (CA)/oxidised (CAO) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

4. Gel Permeation Chromatography

Colominic acid samples (CA and CAO) were dissolved in NaNO3 (0.2M), CH3CN (10%; 5 mg/ml) and were chromatographed on over 2× GMPWXL columns with detection by refractive index (GPC system: VE1121 GPC solvent pump, VE3580 RI detector and collation with Trisec 3 software (Viscotek Europe Ltd). Samples (5 mg/ml) were filtered over 0.45 μm nylon membrane and run at 0.7 cm/min with 0.2M NaNO3 and CH3CN (10%) as the mobile phase.

5. Colominic Acid Stability

Figure 3:
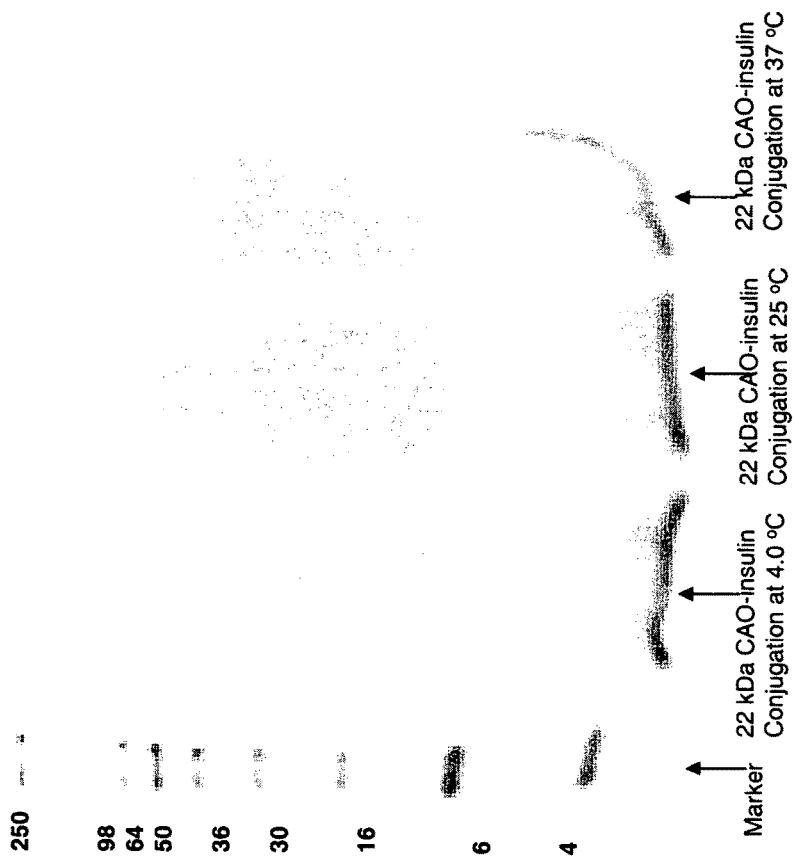
FIG. 3 is an SDS-PAGE of 22 kDa CAO-rh-Insulin conjugates at different temperatures.

The rules for chemistry of the PEGylation cannot be applied to polysialylation as such because of the difference in the physiochemical properties of these molecules. PSA is an acid labile polymer and is stable for weeks around neutral pH (FIG. 3). The results in FIG. 3 show that at pH 6.0 and 7.4 CAO is stable for 8 days, at pH 5.0 there is slow degradation (after 48 hours 92% of initial MW), and at pH 4.0 there is slow degradation (after 48 hours 70% of initial MW). Polysialic acid is highly hydrophilic whereas PEG is an ampiphilic molecule in nature. When the polysialylation is carried out using conditions used for PEGylation, aggregation and precipitation of the proteins is seen in many cases.

6. Preparation of N-Terminal Protein-CA Conjugates with Formulation Additives 6.1 Preparation of Insulin-CA Conjugates (N-Terminal Method)

Insulin (5804 Da) was supplied as white solid. The insulin was dissolved by minimum 100 mM HCl, and then adjusted to the required pH and placed on ice. The amount of CAO to be added for conjugation was calculated based on formula:

$$\text{Weight of CAO} = \frac{\text{Amount of protein (g)}}{\text{(MW of protein)}} \times \text{(MW of CAO)} \times \text{(Molar excess of CAO)}$$

Required amount of CAO was weighed out. CAO was solubilised in 10 mM NaOAc, pH 6.0 gently vortexed the mixture until all the CAO has dissolved and then either filtered into a new container to remove any aggregated/precipitated material. Required amount of insulin protein solution was added to the CAO solution to give a 7.5 molar excess (small scale) and 5 (large scale) of CAO and gently mixed by keeping the reaction mixture on a gentle shaker at 4±1° C. 100 mg/ml NaCNBH3 solution was added in order to have 8 mg/ml in the final reaction mixture, gently mixed and pH of the final reaction mixture was checked, if necessary adjusted the pH to 6.0 with 0.5 M NaOH/HCl at 4±1° C. Finally adjusted the volume of the reaction using 10 mM NaOAc, pH 6.0 to give a protein concentration of 1 mg/ml in the reaction mixture. Tube was sealed and stirred at desired temperature (4±1° C.) for 24 hours. The reaction was stopped by an appropriate method (such as tris(hydroxymethyl)aminomethane buffer pH 7.4) and samples were taken out for SDS-PAGE (using 18% Tris glycine gel), SE-HPLC (superose 12 column) and checked the pH of reaction mixture. To eliminate any precipitate the reaction mixture was centrifuged at 13000 rpm for 5 min before SE-HPLC analysis and purification, preferred buffer for SE-HPLC was 0.1 M Na phosphate (pH 6.9).

6.2 Optimisation

Reductive amination was performed with a range of molecular weights of CAO (10-30 kda) on insulin for N-terminal and random derivatisation. Range of process variables were studied for conjugation reactions: CAO 10-20 (small scale) and 5-10 (large scale) molar excess; reagent=50-100 mM NaCNBH3 reaction buffer=10 mM NaOAc pH 5.5-6.5, temperature=4±1° C., time=16-24 hours etc.

Optimised reaction conditions were found to be as following: CAO=7.5 (small scale) and 5 (large scale) molar excess, reagent=50 mM NaCNBH3, Reaction buffer=10 mM NaOAc pH 5.5, temperature=4±1° C., time=24 hours.

6.3 Purification and Characterization of Insulin-CA Conjugates (N-Terminal Method)

To remove free CAO from the mixture, HIC (HiTrap Butyl FF) was used. Prepare loading solution by diluting the insulin reaction mixture with minimum volume using concentrated $(NH_4)_2SO_4$ (e.g. 3 M), 20 mM $Na_2HPO_4$ (pH 7.4) to give a concentration of 0.8 M $(NH_4)_2SO_4$ in the loading solution. Check pH, should be 7.4 or adjust with 0.5 M HCl/NaOH, the loading solution need be filtered with 0.2 µm membrane filter.

This solution is then loaded on to the HIC column (rate=0.5 ml/min) previously equilibrated with HIC buffer B (20 mM sodium phosphate+0.8 M (NH4)2SO4, pH 7.4). The loading fractions was collected (each fraction 1.5 column volume) and label (L1-Lx) following with washing column with HIC buffer B (at least 5 column volumes; rate=0.5 ml/min; 1.5 column volume fraction) was collected and labelled (W1-Wx). Product with HIC buffer A (10 mM sodium phosphate buffer, pH 7.4) (rate=5 ml/min) was eluted and collected the fractions (1 column volume fraction; 6 column volume) and label (E1-Ex). If two consecutive fractions were absent in protein content (UV280 nm), the next step was carried out. The samples were kept on ice during purification. The protein concentration was analysed by UV (280 nm) (Extinction coefficient of 1 mg/ml of insulin was about 1.043 at 280 nm). The samples taken for SDS-PAGE and SE-HPLC.

HIC fractions containing protein fractions are washed with IEC buffer A (20 mM phosphate buffer, pH 7.4). To remove ammonium sulphate if any in Vivaspin 20 (MW: 5 Kd). Check pH and adjust if required to pH 7.4. Load on the IEC column previously equilibrated with IEC buffer A. A gradient system was applied in the following manner:

Loading: 0.25 ml/min of injected sample in IEC buffer A, washing of 3CV

Washing: Gradient system: IEC buffer A: 90%, AEX buffer B (20 mM phosphate buffer+1M NaCl, pH 7.4): 10%, gradient of 5CV & wash of 3CV, flow rate: 0.25 ml/min IEC buffer A: 68%, IEC buffer B: 32%, gradient of 5 CV & washing of 3CV, flow rate: 0.25 ml/min IEC buffer A: 35%, IEC buffer B: 65%, gradient of 5CV & washing of 3CV, flow rate: 0.25 ml/min IEC buffer A: 0%, IEC buffer B: 100%, gradient of 5CV & washing of 3CV, flow rate: 0.25 ml/min The IEC fractions containing the purified conjugate are combined, washed to remove salt with buffer change of PBS buffer. Adjust pH after removing salt to 7.4. The solution is then concentrated at 4±1° C. and the protein concentration analysed by UV spectroscopy (280 nm). Conjugates were sterile filtered and samples taken for activity assay and for characterisation by SDS-PAGE and SE-HPLC. If required an aliquot was removed for a protein assay and CA assay. The remainder was stored at 4±1° C. until further use and studied for physical stability by SE-HPLC.

The effects of various processes affecting the stability of insulin in solution and the degree of derivatization were studied.

6.4 Preparation of Insulin-14 kDa CA Conjugates (Monodisperse)

Insulin (5808 Da) was supplied as white solid. The insulin was dissolved by adding minimum quantity 100 mM HCl, and then adjusted to the required the pH and placed on ice. The amount of 14 kDa CA to be added for conjugation was calculated based on formula:

$$\text{Weight of 14 kDa CAO} = \frac{\text{Amount of protein (g)}}{\text{(MW of protein)}} \times \text{(MW of CAO)} \times \text{(Molar excess of CAO)}$$

Required amount of 14 kDa CAO was weighed out. 14 kDa CAO was solubilised in 10 mM phosphate buffer, pH 6.0 (20% volume of the final reaction volume was used here), gently vortexed the mixture until all the 14 kDa CAO has dissolved and then either filtered into a new container to remove any aggregated/precipitated material. Required amount of insulin protein solution was added to the 14 kDa CAO solution to give a 7.5 molar excess (small scale) and 5 (large scale) of 14 kDa CAO and gently mixed by keeping the reaction mixture on a gentle shaker at 4±1° C. 100 mg/ml NaCNBH$_3$ solution was added in order to have 63.5 mM or 4 mg/ml in the final reaction mixture, gently mixed and pH of the final reaction mixture was checked, if necessary adjusted the pH to 6.0 with 0.5 M NaOH/HCl at 4±1° C. Finally adjusted the volume of the reaction using 10 mM NaOAc, pH 6.0 to give a protein concentration of 1 mg/ml in the reaction mixture. Tube was sealed and stirred at desired temperature (4±1° C.) for 24 hours. The reaction was stopped by an appropriate method and samples were taken out for SDS-PAGE (using 18% Tris glycine gel), SE-HPLC (superose 12 column) and checked the pH of reaction mixture. To eliminate any precipitate the reaction mixture was centrifuged at 13000 rpm for 5 min before SE-HPLC analysis and purification, preferred buffer for SE-HPLC was 0.1 M Na phosphate (pH 6.9).

6.5 Optimisation

Reductive amination was performed with a range of molecular weights of CA (10-30 kda) on insulin for N-terminal and random derivatisation. Range of process variables were studied for conjugation reactions: CAO 10-20 (small scale) and 5-10 (large scale) molar excess; reagent=50-100 mM NaCNBH3 reaction buffer=10 mM phosphate buffer, pH=5-7.4, temperature=4–37±1° C., time=16-24 hours etc.

Optimised reaction conditions were found to be as following: CAO=7.5 (small scale) and 5 (large scale) molar excess, reagent=63.5 mM NaCNBH$_3$ (, 4 mg/ml). Reaction buffer=10 mM NaOAc pH 6.0, temperature=4±1° C., time=24 hours.

6.6 Purification and Characterization of Insulin-CA Conjugates (N-Terminal Method)

To remove free CAO from the mixture, HIC was used. Prepare loading solution by diluting the insulin reaction mixture with minimum volume using concentrated (NH4)$_2$SO$_4$ e.g. 3 M), 20 mM Na$_2$HPO$_4$, (pH 7.4) to give a concentration of 0.8 M (NH4)$_2$SO$_4$ in the loading solution. Check pH, should be 7.4 or adjust with 0.5 M HCl/NaOH, the loading solution need be filtered with 0.2 mm membrane filter.

This solution is then loaded on to the HIC column (rate=0.5 ml/min) previously equilibrated with HIC buffer B (20 mM sodium phosphate+0.8 M (NH4)2SO4, pH 7.4). Collect the loading fractions (each fraction 1.5 column volume) and label (L1-Lx). Wash column with HIC buffer B (at least 5 column volumes; rate=0.5 ml/min; collect 1.5 column volume fraction) collect fractions and label (W1-Wx). Elute the product with HIC buffer A (10 mM sodium phosphate buffer, pH 7.4) (rate=5 ml/min); collect the fractions (1 column volume fraction; 6 column volume) and label (E1-Ex). If two consecutive fractions were absent in protein content (UV280 nm), the next step was carried out. The samples were kept on ice during purification. The protein concentration was analysed by UV (280 nm) (Extinction coefficient of 1 mg/ml of insulin was about 1.043 at 280 nm). The samples were taken for SDS-PAGE and SE-HPLC.

HIC fractions containing protein fractions are washed with IEC buffer A (20 mM phosphate buffer, pH 7.4). To remove ammonium sulphate if any in Vivaspin 20 (MW: 5 Kd). Check pH and adjust if required to pH 7.4. Load on the IEC column previously equilibrated with IEC buffer A. The gradient system was applied in the following manner:

Loading: 0.25 ml/min of injected sample in IEC buffer A, washing of 3CV

Washing: Gradient system: IEC buffer A: 90%, AEX buffer B (20 mM phosphate buffer+1M NaCl, pH 7.4): 10%, gradient of 5CV & wash of 3CV, flow rate: 0.25 ml/min IEC buffer A: 68%, IEC buffer B: 32%, gradient of 5 CV & washing of 3CV, flow rate: 0.25 ml/min IEC buffer A: 35%, IEC buffer B: 65%, gradient of 5CV & washing of 3CV, flow rate: 0.25 ml/min IEC buffer A: 0%, IEC buffer B: 100%, gradient of 5CV & washing of 3CV, flow rate: 0.25 ml/min The IEC fractions containing the purified conjugate are combined, washed to remove salt with buffer change of PBS buffer. The pH is adjusted after removing salt to 7.4. The solution is then concentrated at 4±1° C. and the protein concentration analysed by UV spectroscopy (280 nm). Conjugate were sterile filtered and samples taken for activity assay and for characterisation by SDS-PAGE and SE-HPLC. If required an aliquot was removed for a protein assay and CA assay. The remainder was stored at 4±1° C. until further use and studied for physical stability by SE-HPLC.

The effects of various processes affecting the stability of insulin in solution and the degree of derivatization were studied.

6.7 SE-HPLC of Insulin Formulations

Figure 8:
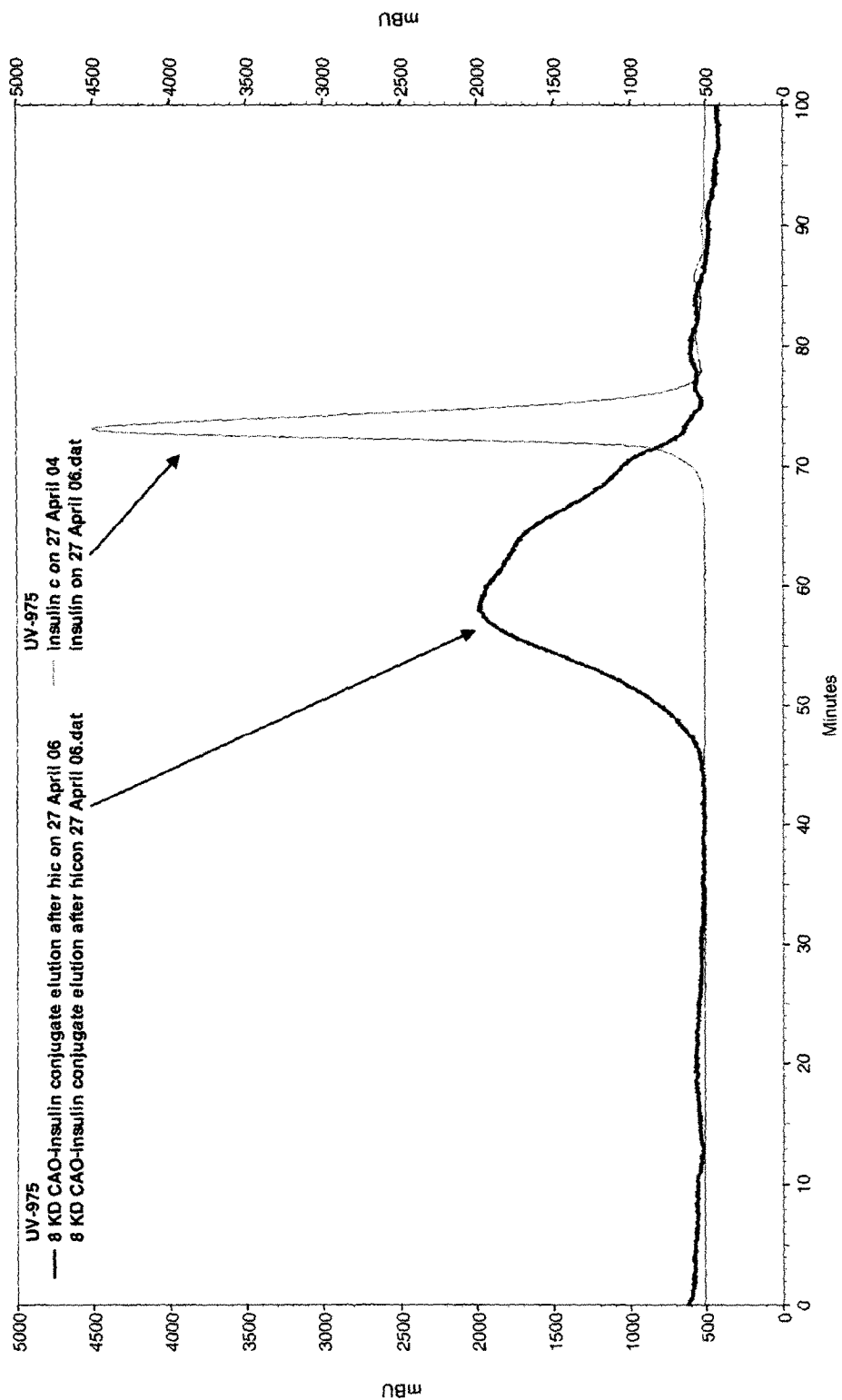
FIG. 8 is an SE-HPLC of 8 kDa CAO-rh-Insulin formulations and insulin.

HPLC was performed on a Liquid Chromatograph (JASCO) equipped with a Jasco, AS-2057 plus autosampler refrigerated at 4° C., and a Jasco UV-975 UV/VIS detector. Data was recorded by EZchrom Elite software on an IBM/PC. The SEC samples were analysed with an isocratic mobile phase of 0.1 M Na phosphate, pH 6.9; on a Superose 12 column (FIG. 8). FIG. 8 shows just one peak at RT=75.408, which was attributed to insulin.

6.8 SDS Polyacrylamide Gel Electrophoresis & Western Blotting

Figure 4:
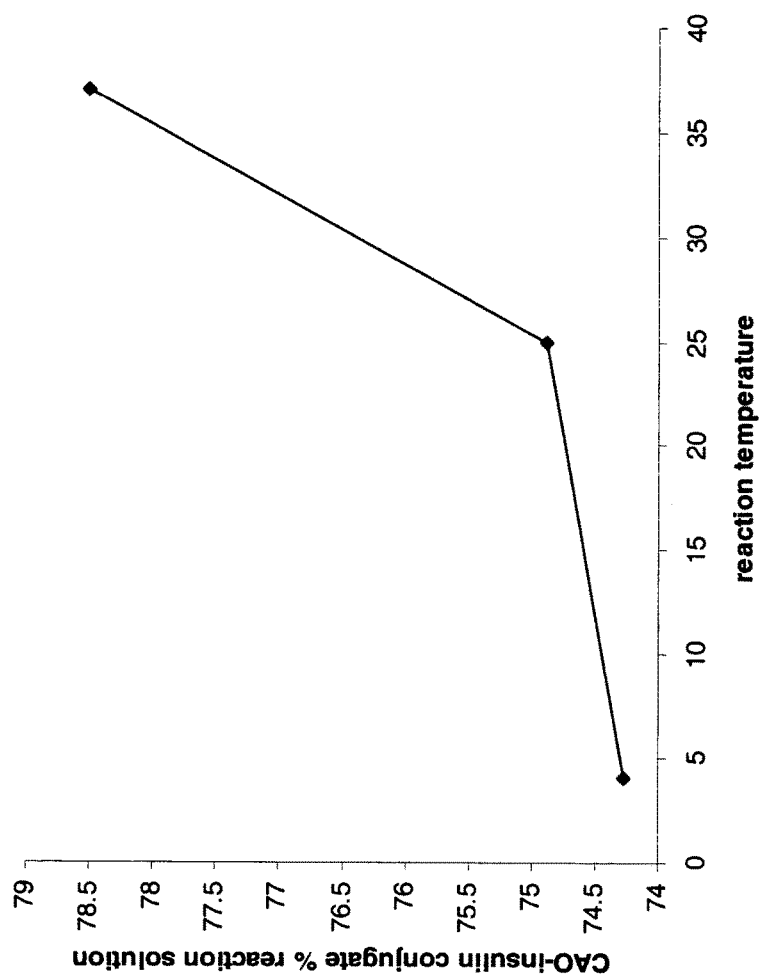
FIG. 4 shows the effects of temperature on the degree of derivatisation.
Figure 5:
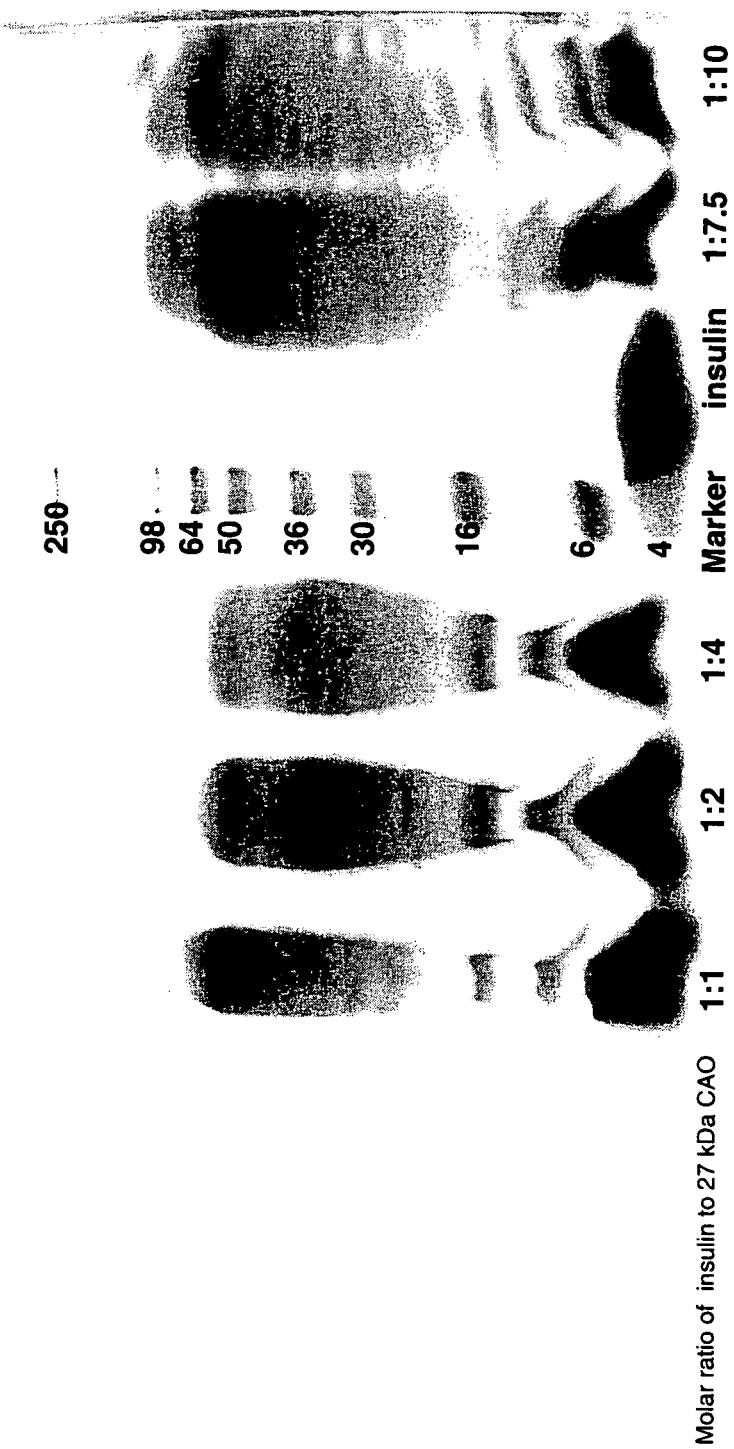
FIG. 5 is an SDS-PAGE of 27 kDa CAO-rh-Insulin conjugations at different molar ratios.
Figure 6:
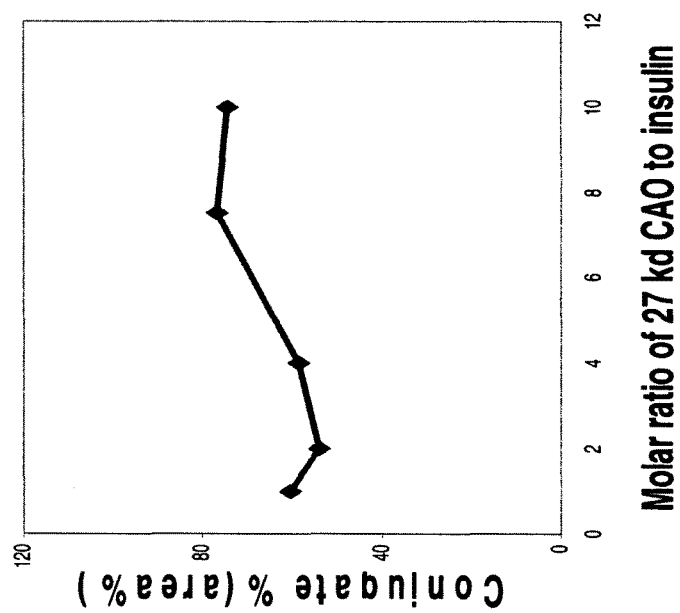
FIG. 6 shows the effects of molar ratio on the degree of derivatisation.
Figure 7:
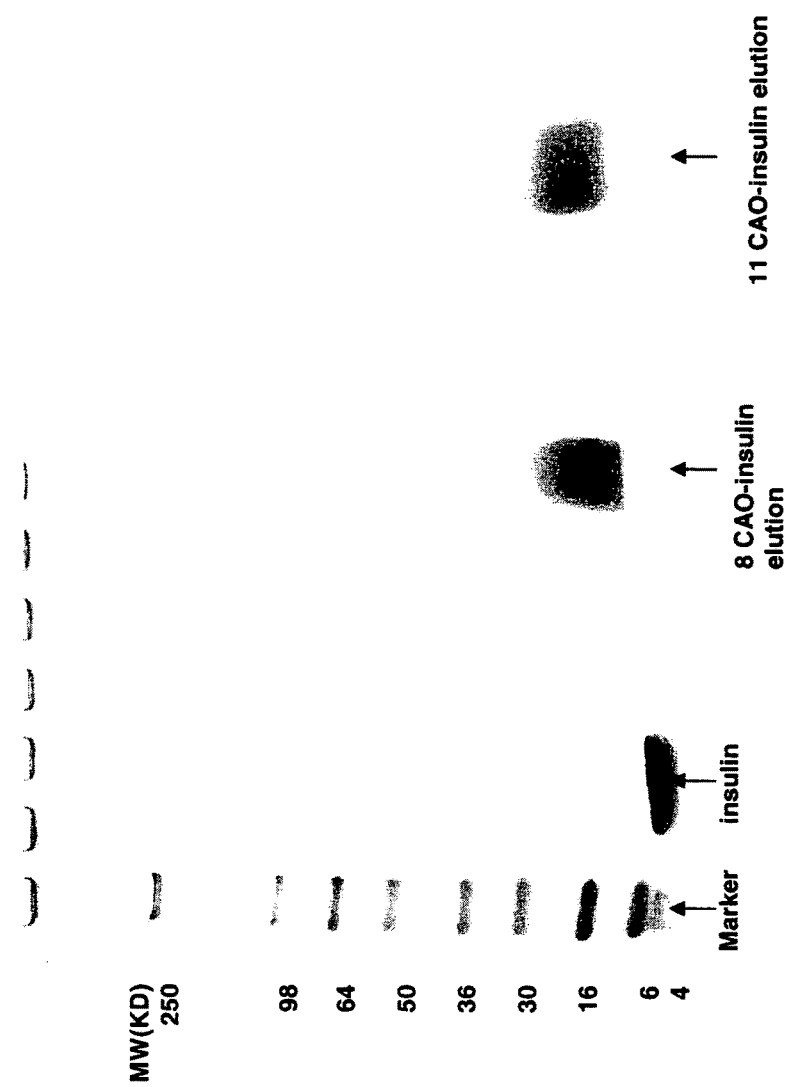
FIG. 7 is an SDS-PAGE of 8 and 11 kDa CAO-rh-Insulin conjugates.

SDS-PAGE was performed using 18% triglyine gels. Samples were diluted with either reducing or non reducing buffer and 5.0 ug of protein was loaded into each well. The gels were run on a triglycerine buffer system and was stained with Coomasie Blue (FIGS. 5 & 7). Western blotting was performed using anti PSA antibody. FIG. 4 shows the SDS-PAGE of insulin formulations (site-specific; N-terminal).

6.9 Isoelectric Focusing (IEF) Gel of 27 and 13 kDa CAO-Insulin

Novex® IEF gel was used to determine differences in insulin and CAO-insulin conjugate isoelectric points. Samples was dissolved to a concentration of 0.5 mg/ml. 5 ul sample was diluted with 5 ul Novex IEF Sample Buffer pH 3-10 and then loaded the protein sample on the gel.

6.10 Stability Studies

Sterile insulin conjugates were stored in PBS buffer; at 4° C. for six weeks. Native-PAGE of the samples was performed every week 6.11 In Vivo Efficacy of Insulin Formulations The in vivo efficacy of insulin formulations was studied in female mice CD-1, 7-8 weeks old, 0.3 IU of protein dose (same activity) was injected in mice subcutaneously. Animals were divided into seven groups of four. insulin formulations were given to each animal of each group in the following manner; insulin (0.3 IU/mouse), Lantus (Aventis) insulin-PSA conjugate (14 KDa), PBS, one drop of blood was taken from each animal and was measured blood glucose by ACCU-CHEK Active (Roche Diagnostics).

Results

Activation of CA and Determination of Degree of Oxidation

Colominic acid (CA) is a linear alpha-2.8-linked homopolymer of N-acetylneuraminic acid (Neu5Ac) residues was used. Exposure of colominic acids to oxidation was carried out for 15 min using 20 mM periodate at room temperature. The integrity of the internal alpha-2.8 linked Neu5Ac residues post periodate treatment was analysed by gel permeation chromatography and the chromatographs obtained for the oxidised (CAO), material was compared with that of native CA. It was found that oxidized and native CA exhibit almost identical elution profiles, with no evidence that the successive oxidation step give rise to significant fragmentation of the polymer chain.

Quantitative measurement of the oxidation state of CA was performed by ferricyanide ion reduction in alkaline solution to ferrocyanide (Prussian Blue) [Park and Johnson, 1949] using glucose as a standard. It shows that the oxidized colominic acid was found to have a greater than stoichiometric (>100%) amount of reducing agent, i.e. 112 mol % of apparent aldehyde content comprising the combined reducing power of the reducing end hemiketal and the introduced aldehyde (at the other end).

Optimisation of Polysialation Reaction

The polysialation conditions were optimized using 1 mg rh-insulin with CAO under variable temperatures and reactant molar ratio, and chain length. The results are shown in FIGS. 5-12. 4° C. would appear to be the optimum temperature for CAO and insulin stability during the reaction. However, at a higher temperature, more conjugation can be attained 7.5:1 of molar ratio of CAO to insulin is more effective.

Table 1 shows the effect of molar ratio on polysialylation.

TABLE 1

| | Well number | | | | | | |
|---|---|---|---|---|---|---|---|
| | 1 | 3 | 5 | 7 | 8 | 11 | 12 |
| Molar ratio | 1:1 | 1:2 | 1:4 | Ma | insulin | 1:7.5 | 1:10 |
| CAO MW | 27 kDa CAO with 100 CHO % | | | | | | |

TABLE 1-continued

| | Well number | | | | | | |
|---|---|---|---|---|---|---|---|
| | 1 | 3 | 5 | 7 | 8 | 11 | 12 |
| Insulin (mg) | 1 | 1 | 1 | | 1 | | 1 |
| CAO (mg) | 4.49 | 8.98 | 17.96 | | 33.675 | | 44.9 |
| Final NaCNBH$_3$ | | | | 4 mg/ml | | | |
| Reaction | | | | 4 | | | |
| pH | | | | 6 | | | |

Figure 9:
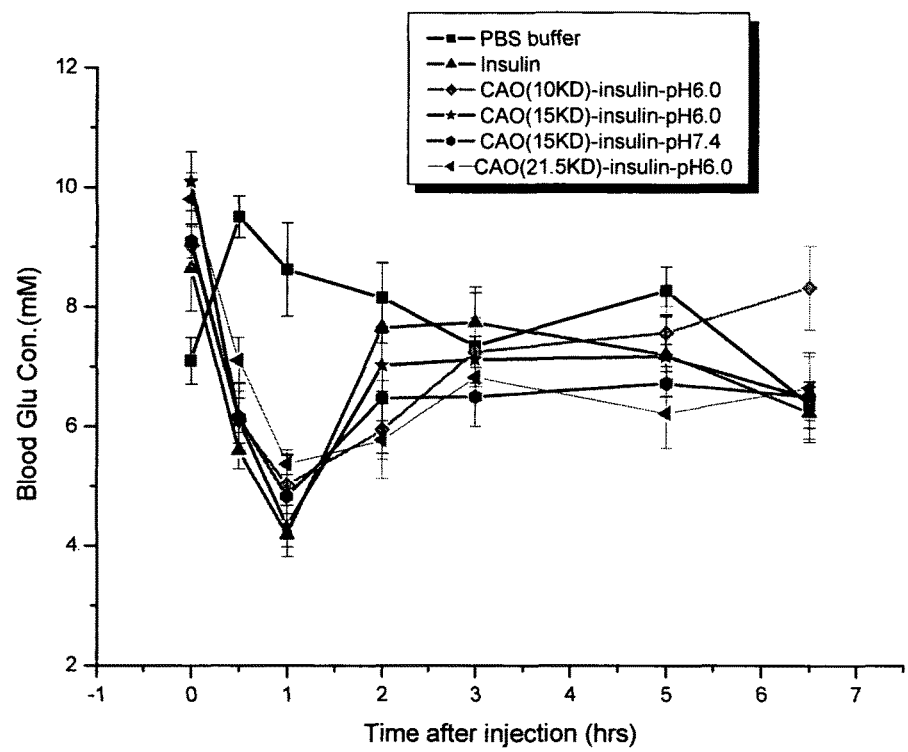
FIG. 9 shows the in vivo efficacy of 10, 15 and 21.5 kDa CAO-insulin formulations.
Figure 10:
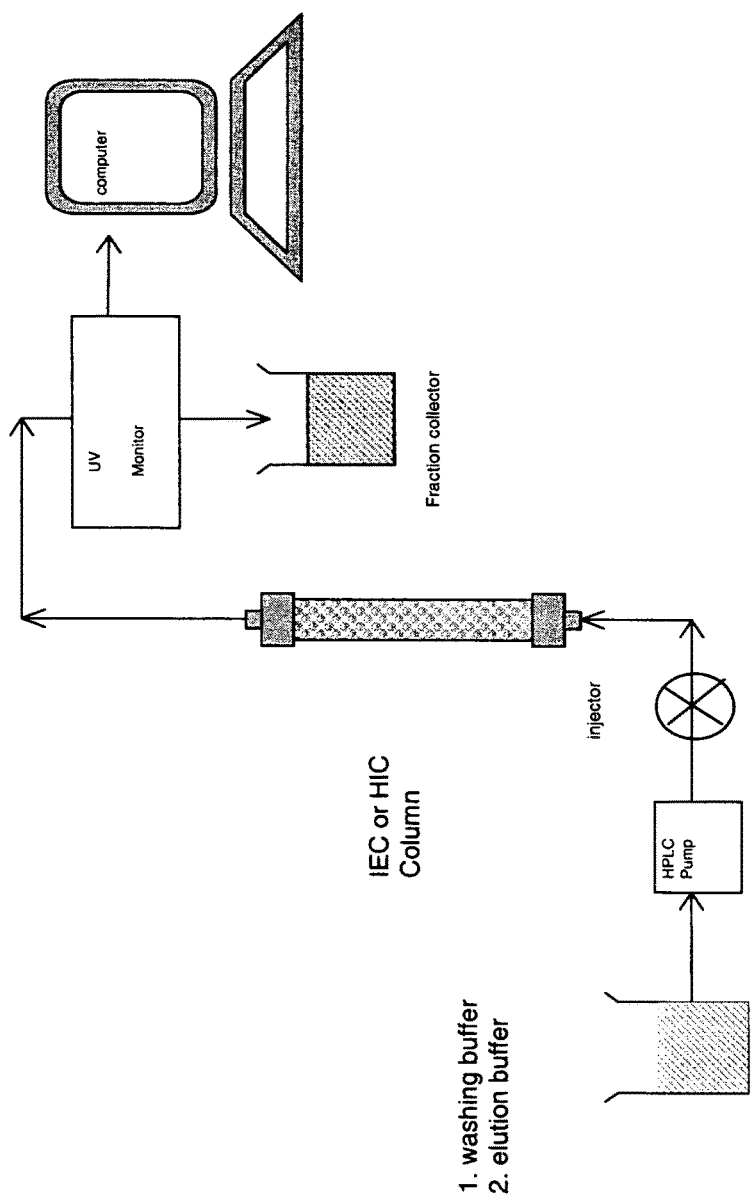
FIG. 10 shows the experimental set-up of preparative HPLC with IEC or HIC for purifying a conjugate.
Figure 11:
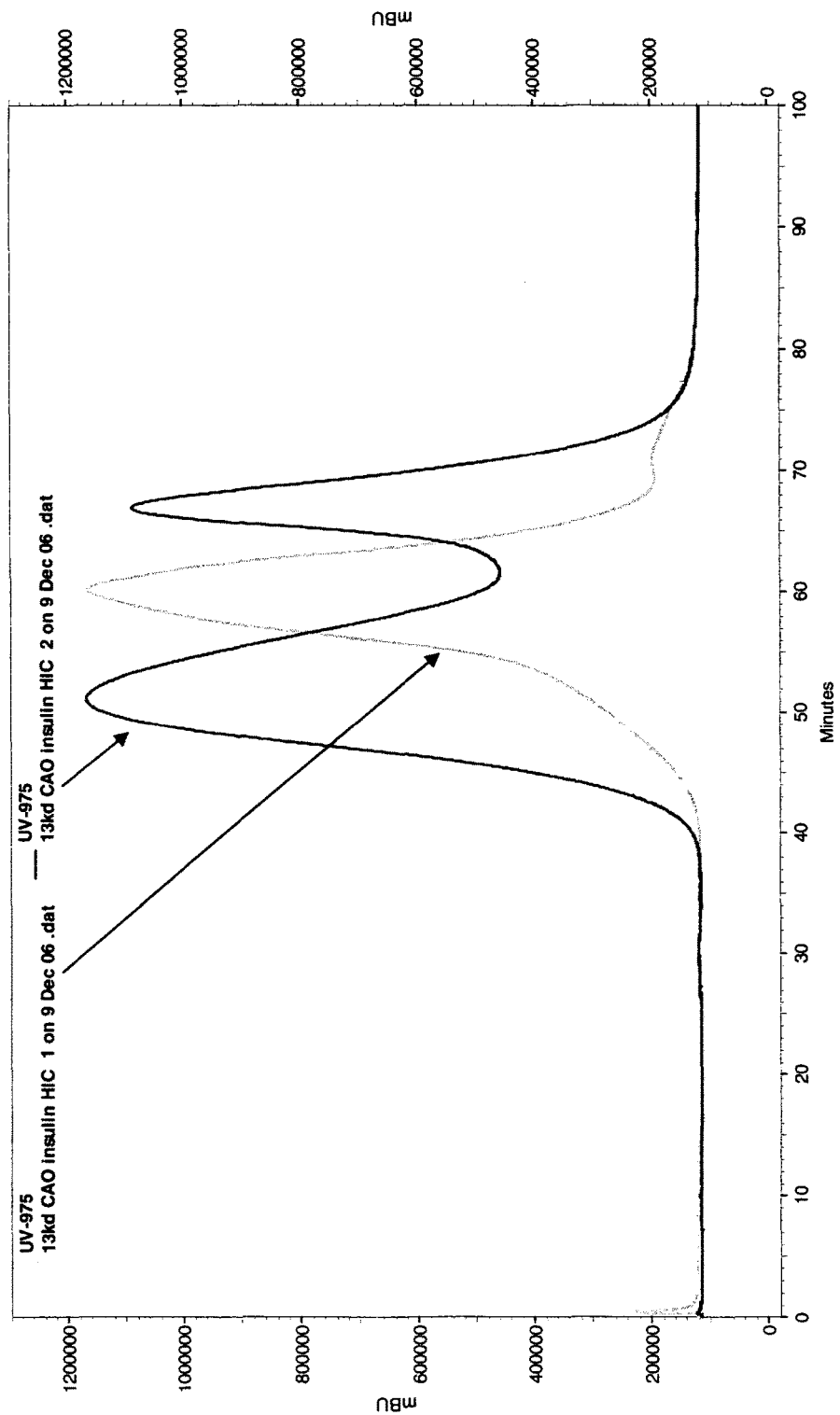
FIG. 11 shows the purification of a CAO-insulin conjugate by Hydrophobic interaction chromatography over a HiTrap Butyl FF column.

Under the influence of PBS control, 21.5 kd CAO-insulin has the most significant effect on the decreasing blood glucose in mice among conjugates used in FIG. 9.

Table 2 shows a T-Test (statistical analysis, paired-test) of different chain CAO-insulin conjugates in vivo efficiency.

TABLE 2

| | Time (minutes) | | | | | | | | |
|---|---|---|---|---|---|---|---|---|---|
| | 0.0 | 32.0 | 64.5 | 99.4 | 170.8 | 230.2 | 303.3 | 358.0 | 1354.9 |
| 13 kDa CAO-insulin | | ** | *** | *** | | | | | |
| 21 kDa CAO-insulin | | | *** | *** | | * | | | |
| 27 kDa CAO-insulin | | ** | *** | ** | | ** | | | ** |
| 32 kDa CAO-insulin | | *** | *** | *** | | | * | | |
| insulin | | *** | *** | *** | | | | | |

Asterisks indicate probability level of the difference between groups against the Tris buffer:
* $P < 0.05$,
** $P < 0.01$,
*** $P < 0.001$

TABLE 3

| | Lantus | 15 KDa CAO-insulin (Sigma) |
|---|---|---|
| 0 | | |
| 30 | *** | ** |
| 60 | *** | *** |
| 90 | ** | *** |
| 120 | * | ** |
| 150 | | * |
| 210 | | |
| 270 | | |
| 330 | | |

Asterisks indicate probability level of the difference between groups against the PBS buffer:
*$P < 0.05$,
**$P < 0.01$,
***$P < 0.001$ The pH effect on in vivo efficiency of 15 kDa CAO-insulin also revealed that pH 6.0 is better than 7.4. Therefore, the afterward experiment was performed at pH 6.0. The data from peptide mapping and Edman degradation further confirmed that the conjugate from pH 6.0 polysialation condition is N-terminally specifically blocked at the B chain of insulin.

Preparation, Purification and Characterisation of Insulin Conjugates

Monodisperse CAO-insulin can be successfully conjugated and highly pure conjugates were purified by scale-up HIC and IEC. The purification efficiency was improved from the IEC and HIC combination set-up with preparative HPLC instrument as demonstrated in FIG. 10.

Figure 12:
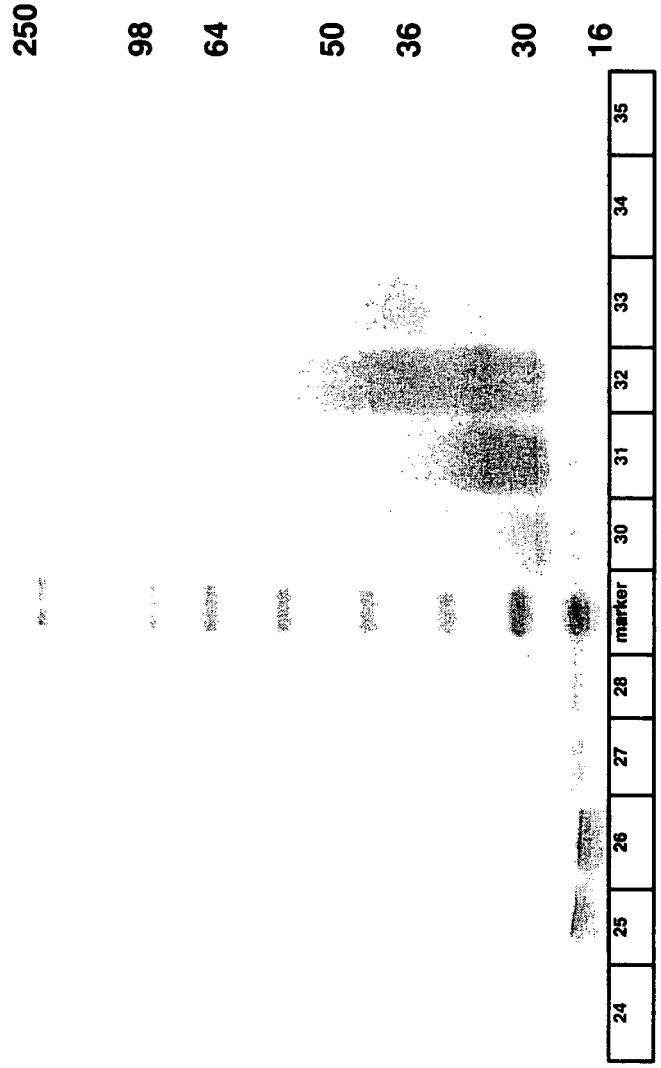
FIG. 12 shows the purification of a CAO-insulin conjugate from HIC peak 2, with 13 kDa CAO as example, by anion exchange chromatography over a Hitrap Q FF column column.

The procedure to prepare and purify colominic acid (CA) conjugates of insulin in an N-terminally selective manner by conducting the reaction at a reduced pH (pH 6.0) and at 4±1° C. is detailed above. This involves conjugation in the presence of sodium cyanoborohydride, followed by purification using hydrophobic interaction chromatography (HIC) to remove free CA (FIG. 11) followed by removal of insulin by ion-exchange chromatography (IEC) (FIG. 12). The low pH was used to favour selective derivatisation at the N-terminus of insulin's B-chain (PheB1), and also in order to minimise aggregation of insulin during the reaction. The composition of the final reaction buffer was 1 mg/ml insulin, 8 mg/ml NaCNBH3 and 5 molar excess CAO in 10 mM NaOAc at pH 6.0.

Figure 13:
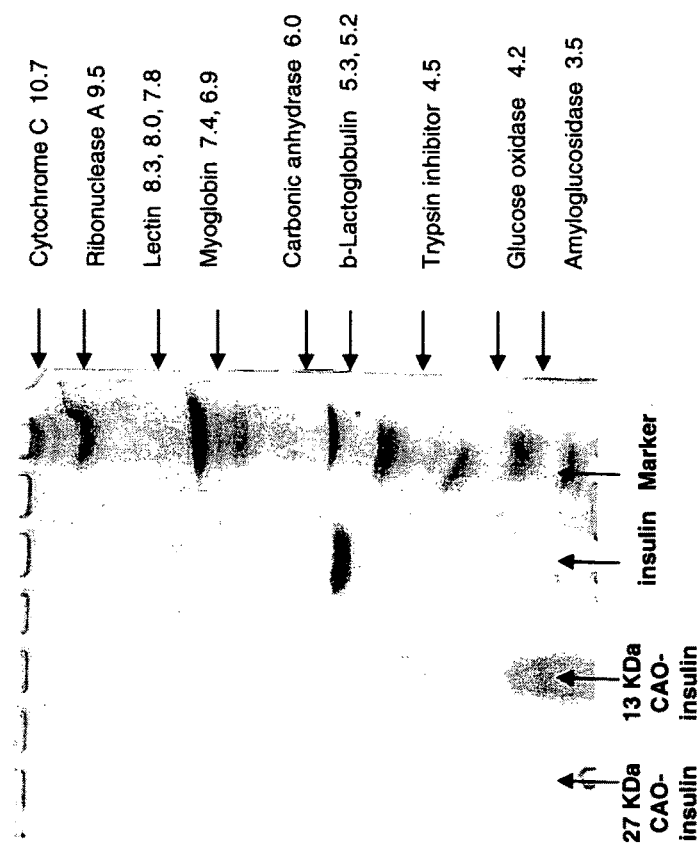
FIG. 13 is an Isoelectric focusing (IEF) gel of a 13 KDa and 27 KDa CAO-insulin conjugate.

Isoelectric focusing (IEF) gels of 13 Kda and 27 Kda CAO-insulin conjugates in FIG. 13 show the conjugate of polysialylated insulin has no fixed isoelectric point (pI).

Formation of the insulin-CA conjugates and stability was confirmed by the SE-HPLC (change of retention time of insulin-PSA as compared to insulin; also co-elution of both moieties); ion exchange chromatography (binding of conjugates on to the IEC column) and polyacrylamide gel electrophoresis (SDS-PAGE; shifting of bands with high m.w. species).

Figure 14:
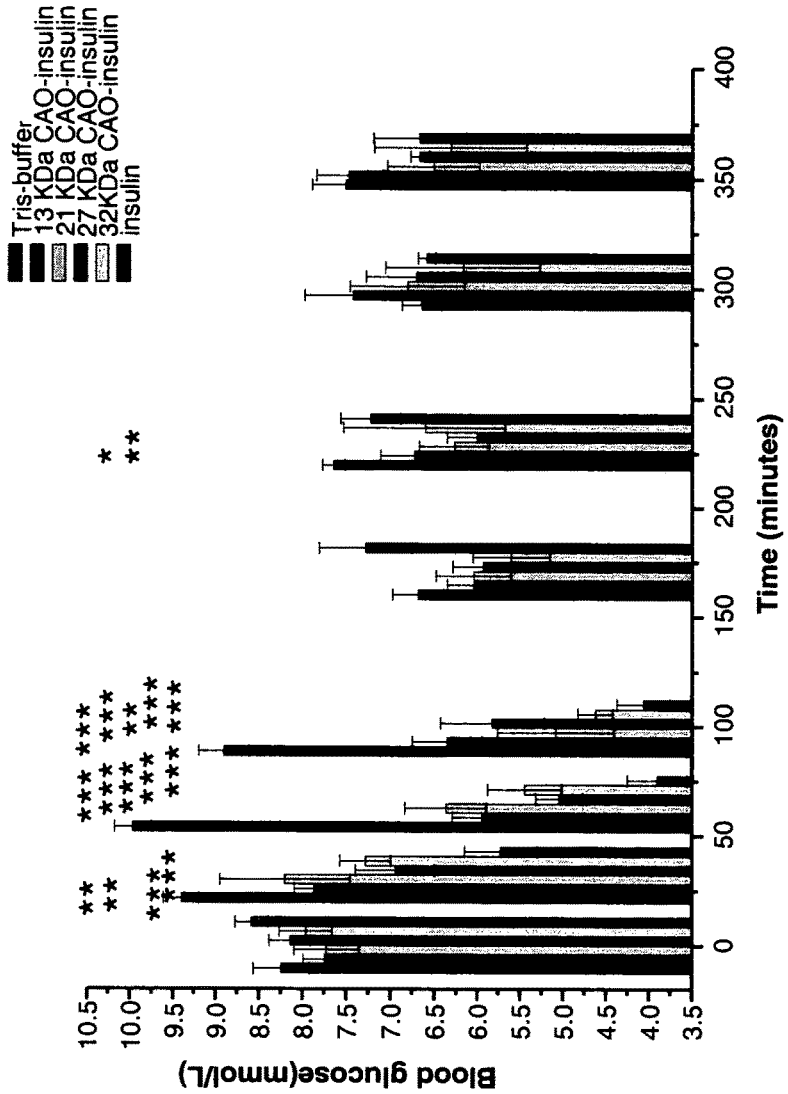
FIG. 14 shows in vivo results of CAO-insulin conjugate in mice.

Insulin conjugates used in the in vivo efficiency (on CD-1 mice, average 25 g) showed superior in vivo efficacy (prolongation) and blunt (peak less profile) as compared to insulin. The prolongation of the blood glucose reducing ability of the conjugates was proportional to chain length of polymer used in the formulation as seen in FIG. 14.

The stability study of 27 KDa CAO-insulin conjugates showed that there was no any degradation during 40 days' 4° C. storage based on the observation from Native-PAGE.

Characterisation of 14 kDa-Insulin Conjugates from Scale-Up Preparation and Purification In the example of insulin as 700 mg start reactant, 230 mg 14 kDa CAO-insulin (protein mass weight) was yielded using scale up column purification.

Figure 15:
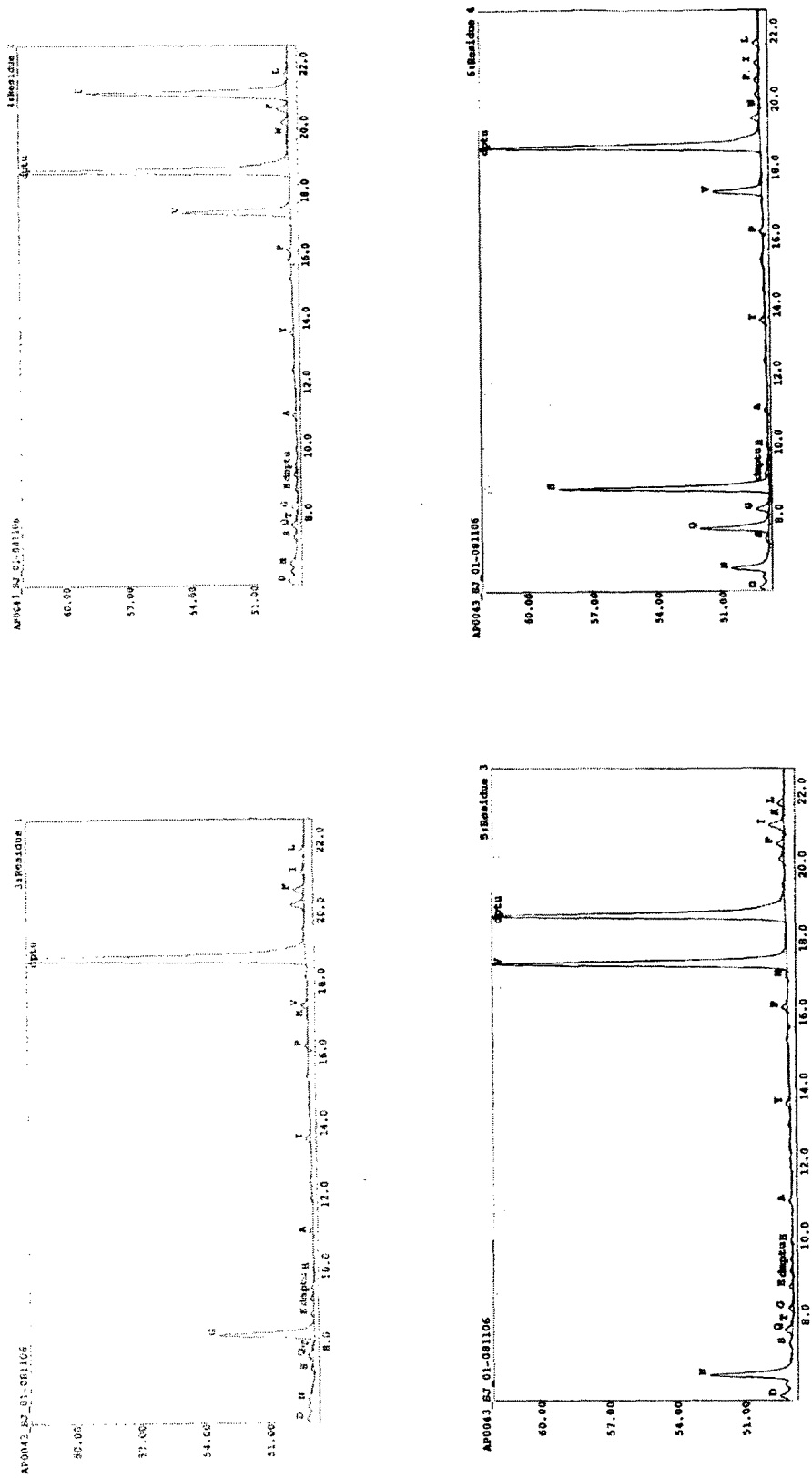
FIG. 15 shows Edman amino acid degradation results.

By comparing chromatograms, changes in amino acid amounts in FIG. 15 reveal the amino acids from N-terminus. The 1 mg/mL aqueous sample in PBS pH 7.4 was diluted× 100 with water. 2 µL of this diluted solution was taken for analysis. In conclusion, the sequence G-I-V-E, identifies the A chain of insulin. The absence of amino acid Phe/Val/Asn/Gln indicated that the B chain of insulin was N-terminally blocked.

The PSA conjugates were found to be active in the in vitro activity assay. In vivo efficacy study shows that PSA-insulin conjugates are vastly superior to insulin.

REFERENCES

Geiger et al. (in D. Branderburg, and A. Wollmer (eds.), 1980, Insulin: Chemistry, Structure, and Function of Insulin and Related Hormones, Walter de Gruyter & Co., New York, P409-415, Ehrat M., Luisi P. L., 1983, Synthesis and spectroscopic characterization of insulin derivatives containing one or two poly(ethylene oxide) chains at specific positions, Biopolymers, 22: P 569-573, Caliceti P, (1999) mprovement of the physicochemical and biopharmaceutical properties of insulin by poly(ethyleneglycol) conjugation, STP Pharma Sciences 9: P 107-113

Uchio, T., Baudys, M., Liu, F., Song, S. C., Kim, S. W., (1999) Site-specific insulin conjugates with enhanced stability and extended action profile., Advanced Drug Delivery Reviews, 35, P 289-306

Hinds K., Koh J. J, Joss L., Liu F., Baudys M. Kim, S. W., (2000). "Synthesis and Characterization of Poly(ethylene glycol)-Insulin Conjugates," Bioconjugate Chem., 11, 195-201

Hinds K. D.; Kim S. W. (2002), Advanced Drug Delivery Reviews, 54: 505-530,

Fernandes, A. I., Gregoriadis, G., Synthesis, characterization and properties of polysialylated catalase, Biochimica et Biophysica Acta, 1293 (1996) 92-96

Fernandes, A. I., Gregoriadis, G., Polysialylated asparaginase: preparation, activity and pharmacokinetics, Biochimica et Biophysica Acta, 1341 (1997) 26-34.

Jain, S. et al Polysialylated insulin: synthesis, characteristaion and biological activity in vivo, Biochimica et Biophysica Acta, 1662 (2003) 42-49;

Gregoriadis, G., McCormack, B., Wang, Z., Lifely, R., Polysialic acids: potential in drug delivery, FEBS Letters, 315 (1993) 271-276.

Park, J. T., Johnson, M. J., A submicrodetermination of glucose, Journal of Biological Chemistry, 181 (1949) 149-151.

Shriner, R. L., Fuson, R. D. C., Curtin, D. Y., Morill, T. C., The Systematic Identification of Organic Compounds, 6th ed., Wiley, New York, 1980.

Svennerholm, L., Quantitative estimation of sialic acid II: A colorimetric resorcinol-hydrochloric acid method, Biochimca et Biophysica Acta, 24 (1957) 604-611.

Wang, W., Instability, stabilization, and formulation of liquid protein pharmaceuticals, International Journal of Pharmaceutics, 185 (1999) 129-188.

The invention claimed is:

1. A method for producing a population of amino-terminal polysialic acid derivatives of insulin the method comprising:
performing a derivatization reaction in a first aqueous solution at pH 6.0 which couples a polysialic acid comprising 2-125 sialic acid units to only the amino-terminal amine of the B-chain of the insulin, thereby producing the population of amino-terminal polysialic acid derivatives of insulin; and
purifying the population of amino-terminal polysialic acid derivatives of insulin using a chromatographical method and eluting in a second aqueous solution at pH 7.4,
wherein at least 85% of the population of amino-terminal polysialic acid derivatives of insulin consists of a polysialic acid coupled only at the amino-terminal amine of the B-chain of the insulin.

2. The method according to claim 1, wherein the polysialic acid has a reactive aldehyde group which reacts with the insulin and the coupling reaction is carried out under reducing conditions.

3. The method according to claim 2, wherein the reactive aldehyde group is at the non-reducing end of the polysialic acid.

4. The method according to claim 2, wherein the reactive aldehyde is at the reducing end of the polysialic acid and the non-reducing end has been passivated such that it does not react with the insulin.

5. The method according to claim 1, wherein the polysialic acid has a reactive aldehyde group and the method comprises:
(a) converting said aldehyde group to an amine;
(b) reacting said amine with a bifunctional reagent comprising at least one functional group selected from N-maleimide, vinylsulphone, N-iodoacetamide, orthopyridyl group and N-hydroxysuccinimide, to form a reaction intermediate; and
(c) reacting the reaction intermediate with the insulin.

6. The method according to claim 1, which is carried out in the presence of a formulation additive.

7. The method according to claim 6, wherein the formulation additive is selected from the group consisting of one or more buffers, stabilizers, surfactants, salts, polymers, metal ions, sugars, polyols and amino acids.

8. The method according to claim 1, wherein the derivatization reaction includes a bifunctional reagent with at least one functional group comprising N-maleimide, vinylsulphone, N-iodoacetamide, orthopyridyl group or N-hydroxysuccinimide.

9. The method according to claim 1, wherein the derivatization reaction is performed under reducing conditions.

10. The method according to claim 9, wherein the derivatization reaction includes hydrogen with catalysts, a hydride, L-ascorbic acid, sodium metabisulphite or L-selectride.

11. The method according to claim 10, wherein the hydride is an alkali metal hydride.

12. The method according to claim 1, wherein the polysialic acid is α-2,8 linked polysialic acid.

13. The method according to claim 1, wherein the polysialic acid comprises 10-80 sialic acid units.

14. The method according to claim 13, wherein the polysialic acid comprises 20-60 sialic acid units.

15. The method according to claim 1, wherein the polysialic acid has a weight average molecular weight in the range about 1 kDa to about 35 kDa.

16. The method according to claim 15, wherein the polysialic acid has a weight average molecular weight in the range about 10 kDa to about 20 kDa.

17. The method according to claim 1, wherein the insulin is derivatised by the polysialic acid at the reducing terminal unit of the polysialic acid.

18. The method according to claim 1, wherein the population of amino-terminal polysialic acid derivatives of insulin has a polydispersity that is less than 1.3.

19. The method according to claim 1, wherein the chromatographical method comprises hydrophobic interaction chromotography, size exclusion chromotography, high performance liquid chromatography or ion exchange chromatography.

20. The method according to claim 1, wherein each amino-terminal polysialic acid derivative of insulin has the general formula (I):

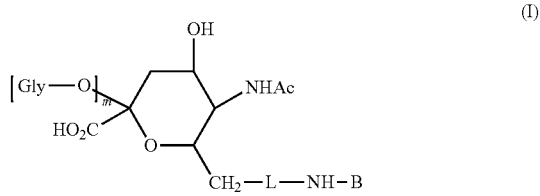

wherein m is any integer from 2 to 125;
HN is derived from $NH_2$ which is the amino terminus of the B-chain of the insulin;
B is insulin;
L is a bond, or a linking group;
GlyO is a sialic acid unit;
wherein the linking group is of the formula: —Y—C(O)—$R^1$—C(O)—, in which $R^1$ is a bifunctional organic radical selected from the group consisting of alkanediyl, arylene, alkarylene, heteroarylene and alkylheteroarylene, any of which may be substituted, and any of which may be interrupted by carbonyl, ester, sulfide, ether, amide and/or amine linkages; and Y is $NR^2$ or $NR^2-NR^2$, wherein $R^2$ is H or $C_{1-6}$alkyl.

21. The method according to claim 20, wherein L is a bond or is:

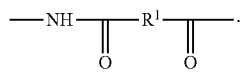

22. The method according to claim 20, wherein m is an integer from 10 to 80.

23. The method according to claim 1, wherein the population of amino-terminal polysialic acid derivatives of insulin is mixed with one or more pharmaceutically acceptable excipients to produce a pharmaceutical composition.

* * * * *